(12) United States Patent
Stivland et al.

(10) Patent No.: US 6,548,010 B1
(45) Date of Patent: Apr. 15, 2003

(54) TRANSITION REGION FOR AN INTRAVASCULAR CATHETER

(75) Inventors: Timothy M. Stivland, Plymouth, MN (US); Michael W. Johnson, Rogers, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/533,403

(22) Filed: Mar. 23, 2000

(51) Int. Cl.[7] .................. B65H 69/08; B29C 65/14; B29C 65/16
(52) U.S. Cl. ............... 264/482; 264/139; 264/248; 264/489; 264/490; 264/491; 264/492; 264/493; 156/158; 156/294; 156/304.1; 156/304.3; 156/304.6
(58) Field of Search ................ 264/248, 249, 264/482, 139, 480, 481, 486, 487, 489, 490, 491, 492, 493; 156/158, 304.1, 304.3, 304.6, 293, 294

(56) References Cited

U.S. PATENT DOCUMENTS

| | | | | |
|---|---|---|---|---|
| 3,924,632 A | * | 12/1975 | Cook ..................... | 604/527 |
| 5,395,335 A | * | 3/1995 | Jang ...................... | 604/102 |
| 5,501,759 A | * | 3/1996 | Forman ................. | 156/272.8 |
| 5,702,439 A | | 12/1997 | Keith et al. ........... | 604/96 |
| 5,791,036 A | * | 8/1998 | Goodin et al. ......... | 29/423 |
| 5,860,963 A | * | 1/1999 | Azam et al. ........... | 604/280 |
| 5,911,715 A | | 6/1999 | Berg et al. ............. | 604/525 |
| 6,042,578 A | * | 3/2000 | Dinh et al. ............. | 604/527 |
| 6,103,037 A | * | 8/2000 | Wilson ................... | 156/158 |

FOREIGN PATENT DOCUMENTS

| | | | |
|---|---|---|---|
| EP | 0 850 653 A2 | 12/1997 | A61M/25/00 |
| WO | WO 98/50098 | 5/1997 | A61M/25/00 |

* cited by examiner

Primary Examiner—Stefan Staicovici
(74) Attorney, Agent, or Firm—Crompton, Seager & Tufte, LLC

(57) ABSTRACT

A method of bonding tubular members comprising the steps of, providing a first generally tubular member having a bonding portion disposed proximate a bonding end thereof, an ancillary end, and a lumen extending therethrough, the first tubular member including a support member encased in a substrate material, the support member having a plurality of filaments providing a second generally tubular member having a bonding portion disposed proximate a bonding end thereof, an ancillary end, and a lumen extending therethrough, stripping a portion of the substrate material of the first tubular member from the filaments of the support member of the first tubular member proximate the bonding portion thereof to create a plurality of exposed filaments, inserting the exposed filaments into the lumen of the second tubular member, positioning the bonding portion of the first tubular member proximate the bonding portion of the second tubular member, and heating the bonding portion of the first tubular member and the bonding portion of the second tubular member to form a bond therebetween.

16 Claims, 19 Drawing Sheets

TRANSITION REGION FOR AN INTRAVASCULAR CATHETER

FIELD OF THE INVENTION

The present invention relates generally to catheters for performing medical procedures. More particularly, the present invention relates to methods of fabricating catheters having one or more guidewire ports and two or more tubular members.

BACKGROUND OF THE INVENTION

Intravascular catheters are currently utilized in a wide variety of minimally-invasive medical procedures. Generally, an intravascular catheter enables a physician to remotely perform a medical procedure by inserting the catheter into the vascular system of the patient at an easily accessible location and navigating the tip of the catheter to the desired target site. By this method, virtually any target site in the patient's vascular system may be remotely accessed, including the coronary, cerebral, and peripheral vasculature.

Typically, the catheter enters the patient's vasculature at a convenient location such as a blood vessel in the neck or near the groin. Once the distal portion of the catheter has entered the patient's vascular system the physician may urge the distal tip forward by applying longitudinal forces to the proximal portion of the catheter. For the catheter to effectively communicate these longitudinal forces it is desirable that the catheter have a high level of pushability and kink resistance particularly near the proximal end.

Frequently the path taken by a catheter through the vascular system is tortuous, requiring the catheter to change direction frequently. In some cases, it may even be necessary for the catheter to double back on itself. In order for the catheter to conform to a patient's tortuous vascular system, it is desirable that intravascular catheters be very flexible, particularly near the distal end.

While advancing the catheter through the tortuous path of the patients vasculature, physicians often apply torsional forces to the proximal portion of the catheter to aid in steering the catheter. To facilitate the steering process, the distal portion of the catheter may include a plurality of bends or curves. Torsional forces applied on the proximal end must translate to the distal end to aid in steering. It is therefore desirable that the proximal portion of an intravascular catheter have a relatively high level of torquability to facilitate steering.

After the intravascular catheter has been navigated through the patient's vascular system so that its distal end is adjacent the target site, the catheter may be used for various diagnostic and/or therapeutic purposes. One example of a diagnostic use for an intravascular catheter is the delivery of radiopaque contrast solution to enhance fluoroscopic visualization. In this application, the intravascular catheter provides a fluid path leading from a location outside the body to a desired location inside the body of a patient. In order to maintain a fluid path, it is desirable that intravascular catheters be sufficiently resistant to kinking. In addition, because such fluids are delivered under pressure, it is also desirable that intravascular catheters be sufficiently resistant to bursting or leaking.

Examples of therapeutic purposes for intravascular catheters include percutaneous transluminal angioplasty (PTA) and percutaneous transluminal coronary angioplasty (PTCA). These angioplasty techniques typically involve the use of a guide catheter and a balloon catheter. During these procedures, the distal end of the guide catheter is typically inserted into the femoral artery located near the groin of the patient. The guide catheter is urged through the vasculature of the patient until its distal end is proximate the restriction. In many cases, the distal end of the guide catheter is positioned in the ostium of the coronary artery. The balloon catheter may then be fed through a lumen in the guide catheter such that the balloon is positioned proximate a restriction in a diseased vessel. The balloon is then inflated and the restriction in the vessel is opened. In this application, it is desirable that the guide catheter provide a low friction path for the balloon catheter. The balloon is inflated by urging a liquid though the elongate shaft of the balloon catheter and into the balloon. In this application, the balloon catheter must provide an unobstructed path for the inflation fluid. It is also desirable that the catheter be substantially free of leaks.

As described at length above, it is desirable to combine a number of performance features in an intravascular catheter. It is desirable that the catheter have a relatively high level of pushability and torqueability, particularly near its proximal end. It is also desirable that a catheter be relatively flexible, particularly near it's distal end. The need for this combination of performance features is often addressed by building a catheter which has two or more discrete tubular members having different performance characteristics. For example, a relatively flexible distal section may be spliced to a relatively rigid proximal section. When a catheter is formed from two or more discrete tubular members, it is often necessary to form a bond between the distal end of one tubular member and the proximal end of another tubular member.

Intravascular catheters are often used in conjunction with a guidewire. When this is the case, the guidewire may be advanced through the patient's vasculature until its distal tip has reached a desired target location. Once the distal portion of the guidewire is proximate the desired location, the catheter may be threaded onto the guidewire and urged distally until the distal end of the catheter is proximate the target location.

Intravascular catheters adapted for use with a guidewire typically fall into one of two categories: the over-the-wire category or the single operator exchange (SOE) category. An over-the wire type of catheter includes a guidewire lumen extending from the distal tip of the catheter to the proximal end of the catheter. Whereas, a single operator exchange catheter typically includes a relatively short guidewire lumen proximate the distal end of the catheter.

Single operator exchange catheters were developed in response to difficulties encountered when exchanging over-the-wire catheters. Generally, it is desirable to leave the guidewire in place while a first catheter is withdrawn from the patient and replaced with a second catheter. Maintaining the position of the guidewire tip during the procedure aids the physician in quickly positioning the distal end of the second catheter proximate the target area.

In order to keep the guidewire tip near the target area, the guidewire must be held in place throughout the catheter exchange procedure. A portion of the guidewire is typically grasped by the physician in order to withdraw the first catheter while maintaining distal end of the guidewire in the desired position. To properly anchor the guidewire, a portion of the guidewire must be exposed at all times so it is available for the physician to grasp. In the case of an over-the-wire catheter, this requires that the length of the guidewire extending beyond the patient's body be longer than the catheters. In some cases, length must be added to the guidewire using a guidewire extension. In many cases intravascular catheters are longer than 200 cm. Correspondingly, there may be more than 200 cm of wire extending from the patient. Managing this length of wire during a catheter exchange procedure is awkward, and typically requires two persons. In particular, contamination must be avoided by assuring that the guidewire is not dropped from the sterile field.

An SOE catheter, on the other hand, has a relatively short guidewire wire lumen proximate its distal tip. The length of guidewire extending beyond the body of the patient need only be slightly longer than the guidewire lumen of the catheter. The physician may anchor or hold the guidewire as the first catheter is removed from the body with the exchange occurring over the shorter guidewire lumen. The guidewire lumen of an SOE catheter typically includes a distal guidewire port disposed at the distal tip of the catheter and a proximal guidewire port disposed proximally of the distal end of the catheter. It is desirable to fabricate an SOE catheter, to include a proximal guidewire port, while maintaining the other desirable performance features described previously.

SUMMARY OF THE INVENTION

The present invention relates generally to catheters for performing medical procedures. More particularly, the present invention relates to methods of fabricating catheters having one or more guidewire ports and two or more tubular members.

A catheter assembly in accordance with the present invention includes an elongate shaft having a proximal shaft portion, a middle shaft portion, and a distal shaft portion. The proximal shaft portion, the middle shaft portion, and the distal shaft portion each have a proximal end and a distal end. The distal end of the proximal shaft portion is fixed to the proximal end of the middle shaft portion. Likewise, the distal end of middle shaft portion is fixed to the proximal end of distal shaft portion at a transition region.

A presently preferred embodiment of a catheter in accordance with the present invention includes a proximal guidewire port disposed proximate the transition region. The catheter further includes a distal guidewire port disposed proximate the distal end of the elongate shaft. The elongate shaft of the catheter includes a plurality of walls defining a guidewire lumen which is in fluid communication with the proximal guidewire port and the distal guidewire port.

The elongate shaft also includes a plurality of walls defining an inflation lumen. The inflation lumen is in fluid communication with a balloon disposed at the distal end of the elongate shaft of the catheter. The inflation lumen is also in fluid communication with a port of a hub assembly disposed about the elongate shaft of the catheter proximate its proximal end. A fluid source may be coupled to the port of the hub assembly. The balloon may be inflated by urging fluid from the fluid source into the balloon via the inflation lumen.

The inflation lumen an the guidewire lumen both pass through the transition region of the catheter. In a presently preferred embodiment, the distal end of middle shaft portion is fixed to the proximal end of distal shaft portion proximate the transition region of the catheter. Methods of fabricating a catheter having such a transition region are disclosed.

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention. Examples of constructions, materials, dimensions, and manufacturing processes are provided for various elements. Those skilled in the art will recognize that many of the examples provided have suitable alternatives which may be utilized.

Figure 1:
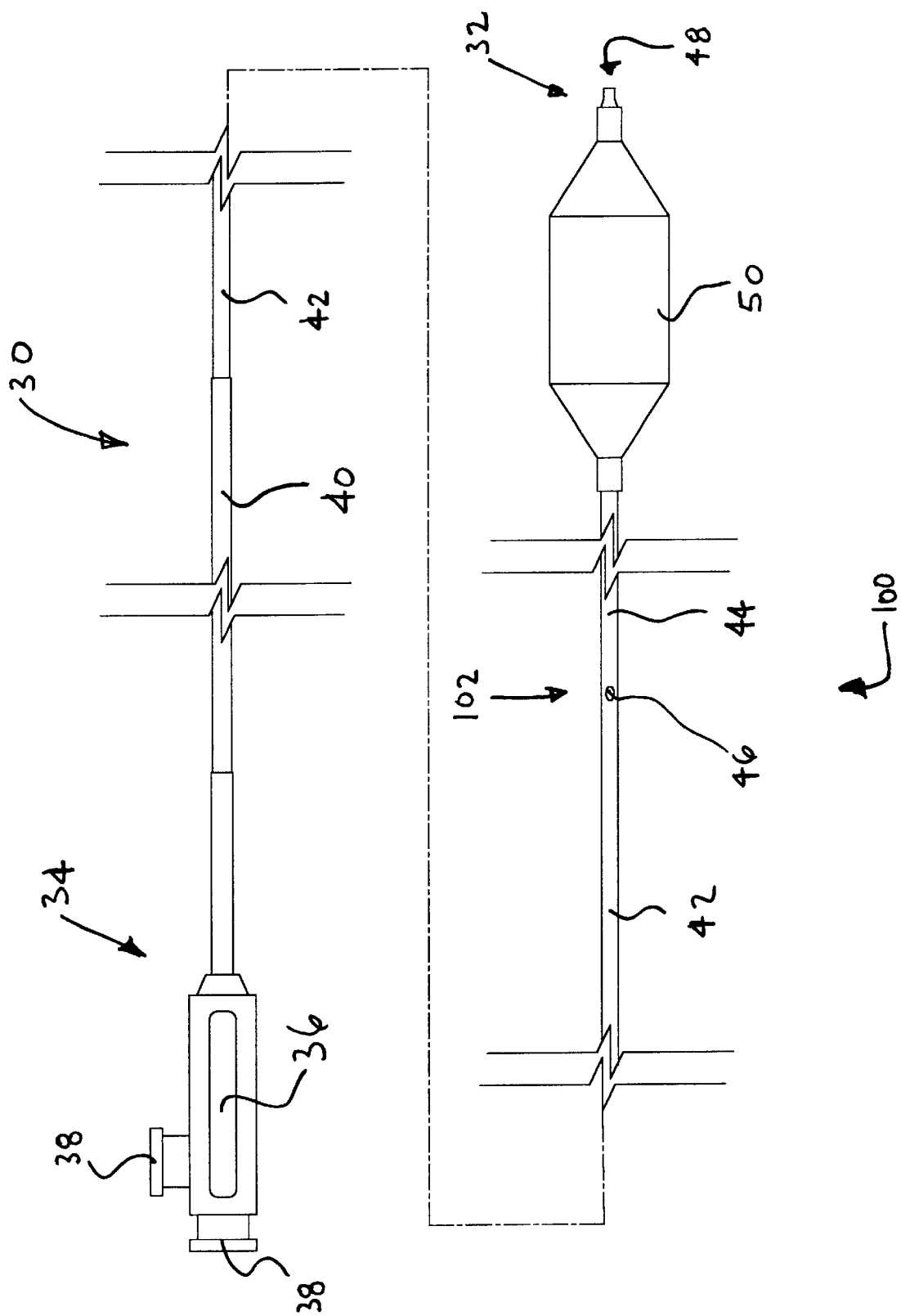
FIG. 1 is a plan view of a catheter in accordance with an exemplary embodiment of the present invention.

FIG. 1 is a plan view of a catheter 100 in accordance with an exemplary embodiment of the present invention. Catheter 100 includes an elongate shaft 30 having a distal end 32 and a proximate end 34. A hub assembly 36 is disposed about elongate shaft 30, proximate proximal end 34 thereof. Hub assembly 36 includes a plurality of ports 38.

Elongate shaft 30 includes a proximal shaft portion 40, a middle shaft portion 42, and a distal shaft portion 44. Proximal shaft portion 40, middle shaft portion 42, and distal shaft portion 44 each have a proximal end and a distal end. As shown in FIG. 1, the distal end of proximal shaft portion 40 is fixed to the proximal end of middle shaft portion 42. Likewise, the distal end of middle shaft portion 42 is fixed to the proximal end of distal shaft portion 44 proximate a transition region 102. Those of skill in the art will appreciate that catheter 100 may include more or less than three shaft portions without deviating from the spirit and scope of the present invention.

In the embodiment of FIG. 1, catheter 100 includes a proximal guidewire port 46 disposed proximate transition region 102. Catheter 100 also includes a distal guidewire port 48 disposed proximate distal end 32 of elongate shaft 30. Elongate shaft 30 includes a plurality of walls defining a guidewire lumen 104 (not shown) which is in fluid communication with proximal guidewire port 46 and distal guidewire port 48.

Elongate shaft 30 also includes a plurality of walls defining an inflation lumen 106 not shown. Inflation lumen 106 is in fluid communication with port 38 of hub 36 and a balloon 50 disposed about elongate shaft 30 proximate distal end 34. Port 38 of hub 36 is adapted to couple with a fluid source. Balloon 50 may be inflated by urging fluid from the fluid source into balloon 50 via inflation lumen 106. Catheter 100 of FIG. 1 is a type of catheter which may be generally referred to as a balloon catheter. Those of skill in the art will appreciate that methods and devices in accordance with the present invention may be used to fabricate other types of catheter.

Those of skill in the art will appreciate that proximal shaft portion 40, middle shaft portion 42, and distal shaft portion 44 may be comprised of many materials without deviating from the spirit and scope of the present invention. An exemplary embodiment of a shaft portion 52 is illustrated in FIG. 2.

Figure 2:
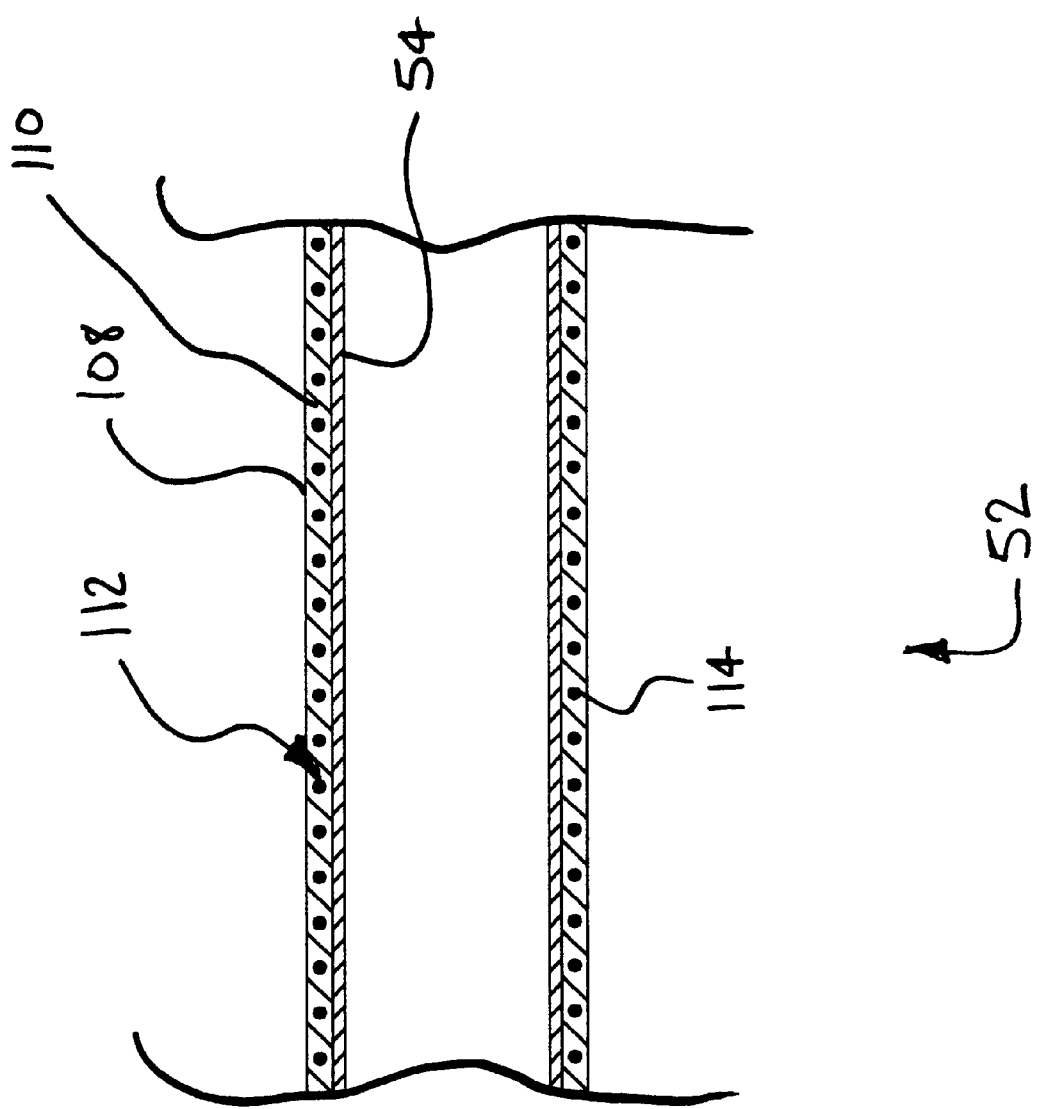
FIG. 2 is a cross sectional view of an exemplary embodiment of a generally tubular shaft.

FIG. 2 is a cross sectional view of a shaft portion 52. As shown in FIG. 2, shaft portion 52 is comprised of an inner tube 54 which is overlaid by a support member 112. An outer layer 108 of a jacket material 110 overlays support member 112. Jacket material 110 of outer layer 108 is also disposed within a plurality of interstitial spaces defined by support member 112. In the embodiment of FIG. 2, support member 112 is comprised of a plurality of filaments 114. In a preferred embodiment, filaments 114 are comprised of stainless steel wire, wound in a braided pattern around inner tube 54. Those of skill in the art will appreciate that other embodiments of support member 112 are possible without deviating from the spirit and scope of the present invention. For example, support member 112 may be comprised of a plurality of polymer filaments braided or knitted together. By way of a second example, support member 112 may be comprised of polymer filaments wound in a spiral pattern around inner tube 54.

In a presently preferred embodiment, outer layer 108 is comprised of polyether block amide (PEBA). Polyether block amide is commercially available from Atochem Polymers of Birdsboro, Pa. under the trade name PEBAX. Outer layer 108 may be fabricated using an extrusion process. In this process, molten PEBA is extruded onto the combined layers of inner tube 54 and support member 112. When this process is used, the material of outer layer 108 fills any interstitial spaces in support member 112.

It is to be understood that other manufacturing processes may be used without departing from the spirit and scope of the present invention. Outer layer 108 may also be comprised of other materials without departing from the spirit of scope of this invention. Examples of materials which may be suitable in some applications include: polyethylene (PE), polypropylene (PP), polyvinylchloride (PVC), polyurethane, and polytetrafluoroethylene (PTFE).

Figure 3:
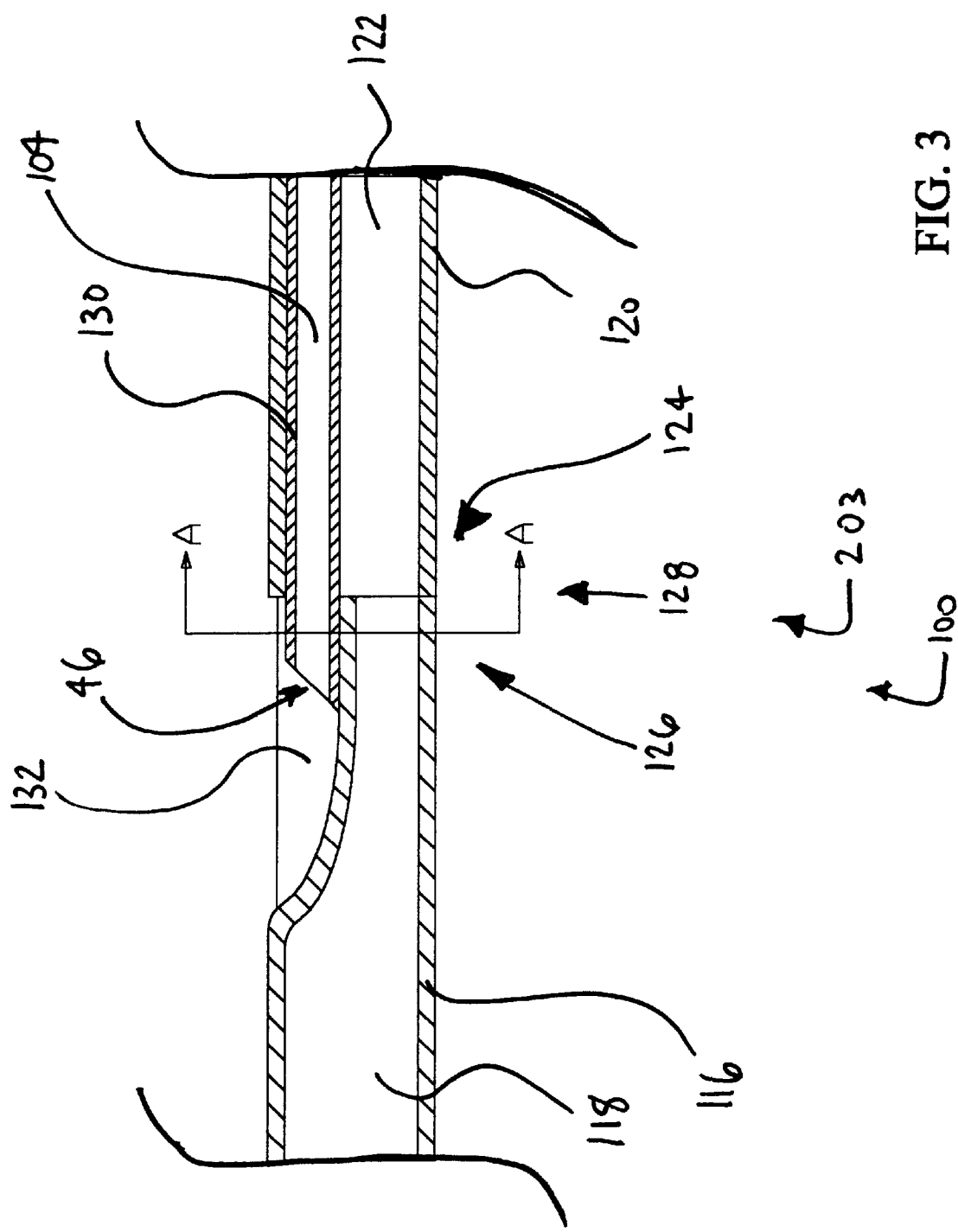
FIG. 3 is a cross sectional view of an assembly including first shaft portion having a first lumen and second shaft portion having a second lumen.

FIG. 3 is a cross sectional view of an assembly 203 including first shaft portion 116 having a first lumen 118 and second shaft portion 120 having a second lumen 122. In one method in accordance with the present invention, assembling first shaft portion 116 and second shaft portion 120 as shown in FIG. 3 is one step in a method used to fabricate a transition region 102 of a catheter 100. A method in accordance with the present invention may also include the step of applying heat to form a fused region bonding first shaft portion 116 and second shaft portion 120.

As shown in FIG. 3, a proximal end 124 of second shaft portion 120 is disposed proximate a distal end 126 of first shaft portion 116 forming a joint 128. Joint 128 of FIG. 3 may be generally referred to as a butt joint. An inner tubular member or inner 130 is disposed proximate a crimp 132 formed in first shaft portion 116. As show in FIG. 3, a portion of inner 130 is disposed within second lumen 122 defined by second shaft portion 120. First lumen 118 of first shaft portion 116 is also visible in FIG. 4. In a presently preferred embodiment, inner 130 defines a proximal guidewire port 46, a guidewire lumen 104, and a distal guidewire port 48 (not shown) of catheter 100.

Figure 4:
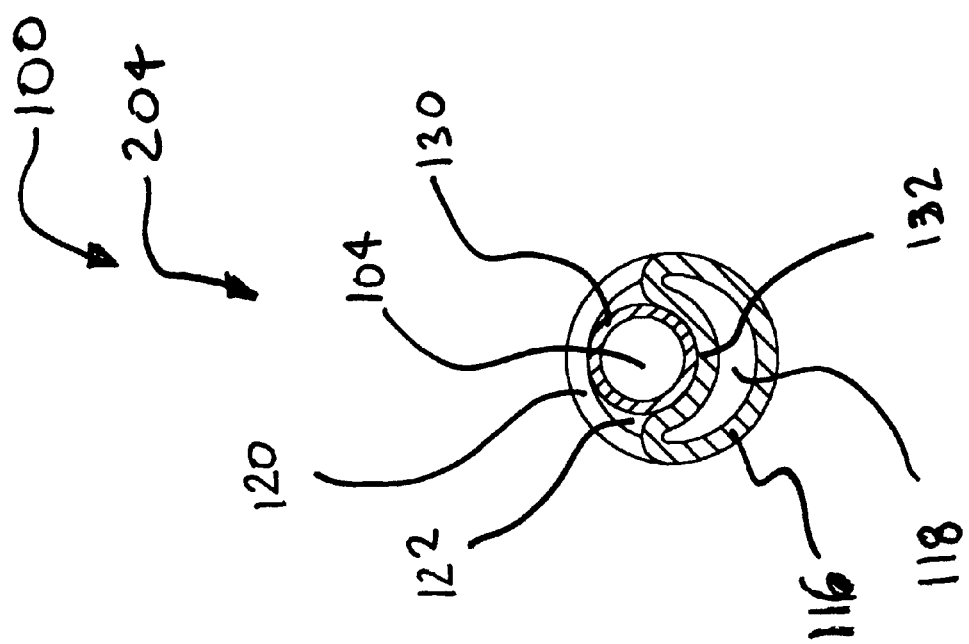
FIG. 4 is a cross sectional view of the assembly of FIG. 3 taken along line A—A shown in FIG. 3.

FIG. 4 is a cross sectional view of assembly 204 taken along line A—A shown in FIG. 3. The position of inner 130 relative to crimp 132 of first shaft portion 116 is best shown in FIG. 4. A guidewire lumen 104 defined by inner 130 is also shown in FIG. 4. It may be appreciated that inflation lumen 106 of catheter 100 may include second lumen 122 defined by second shaft portion 120 and a first lumen 118 defined by first shaft portion 116.

As mentioned previously, in one method in accordance with the present invention, assembling first shaft portion 116 and second shaft portion 120 as shown in FIG. 3 may be one step in a method used to fabricate transition region 102 of catheter 100. A method in accordance with the present invention may also include the step of selectively heating a portion of assembly 204 to create a fused region 134. In a presently preferred method, the selective heating of a portion of assembly 204 is accomplished by illuminating a portion of assembly 204 with a LASER (light amplification by stimulated emission of radiation) beam. In a presently most preferred method, assembly 204 is rotated while a portion thereof is illuminated with a LASER beam.

Figure 5:
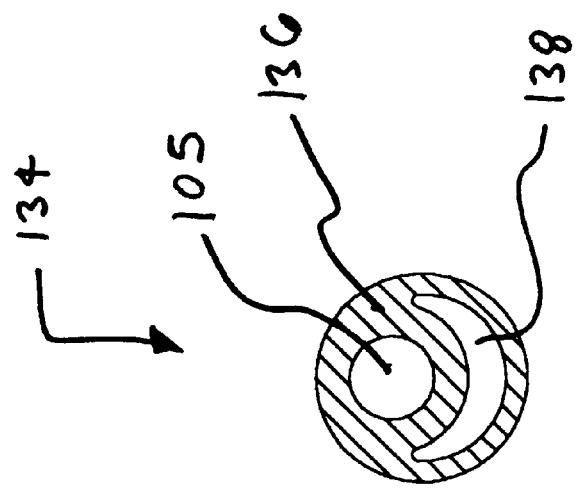
FIG. 5 is a cross sectional view of the assembly of FIG. 4 after a portion of the assembly has been fused in accordance with a method of the present invention.

FIG. 5 is a cross sectional view of assembly 204 of FIG. 4 after a portion of the assembly has been fused in accordance with a method of the present invention. As shown in FIG. 4, a fused region 134 comprising fused material 136 has been formed. A transition region guidewire lumen 105 and a transition region inflation lumen 138 are defined by fused material 136. In a presently preferred embodiment, transition region inflation lumens 138 is in fluid communication with first lumen 118 of first shaft portion 116 and second lumen 122 of second shaft portion 120. It may be appreciated that, transition region inflation lumen 138, first lumen 118, and second lumen 122 may all form a portion of inflation lumen 106 of catheter 100.

Figure 6:
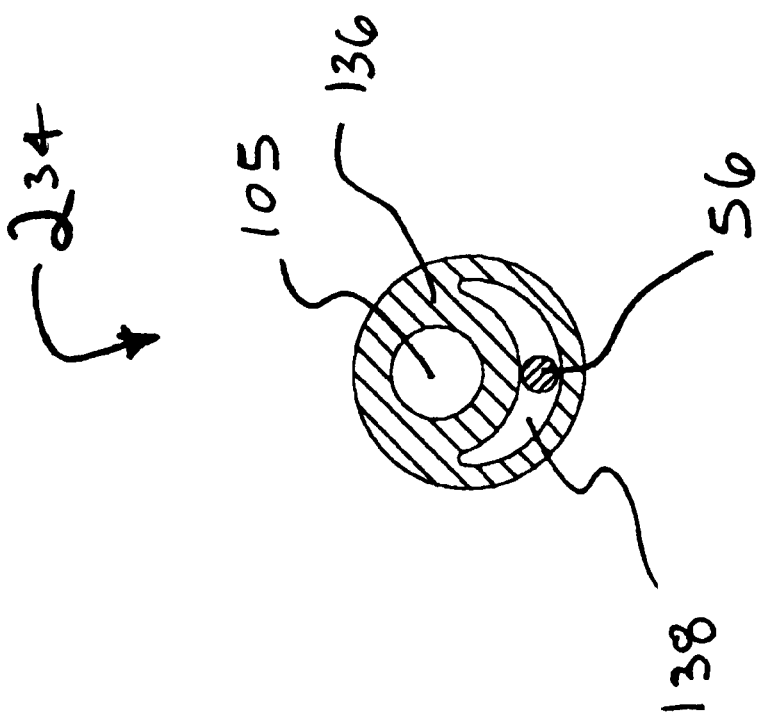
FIG. 6 is a cross sectional view of an additional embodiment of a fused region of a transition region of a catheter.

FIG. 6 is a cross sectional view of an additional embodiment of a fused region 234. In the embodiment of FIG. 6, a core wire 56 is disposed within transition region inflation lumen 138. In a presently preferred embodiment, core wire 56 passes through transition region 102 and is adapted to provide a desired stiffness to transition region 102 of catheter 100. Core wire 56 may include one or more tapered regions along its length. The tapered regions of core wire 56 may provide desirable variations in stiffness.

Figure 7:
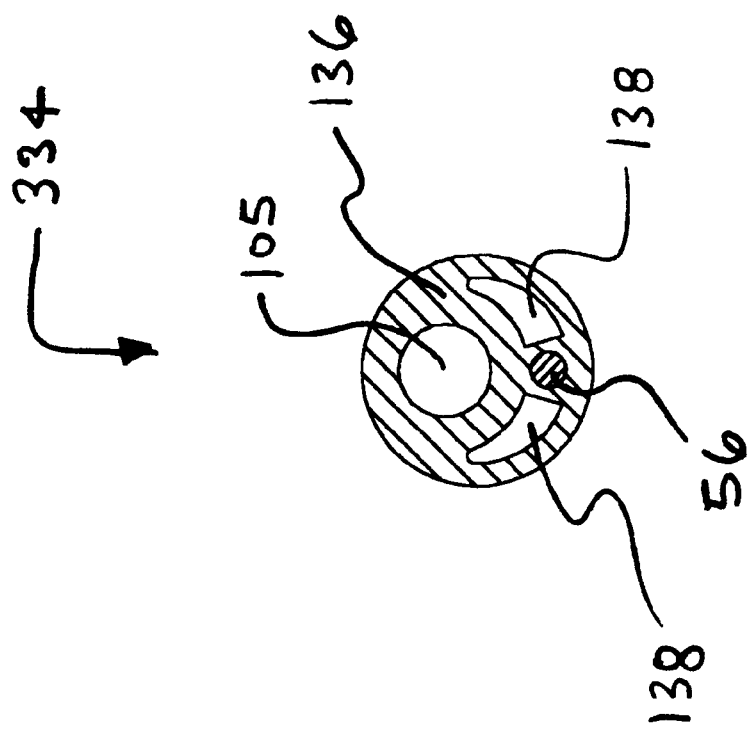
FIG. 7 is a cross sectional view of another embodiment of a fused region of a transition region of a catheter.

FIG. 7 is a cross sectional view of an additional embodiment of a fused region 334. In the embodiment of FIG. 7, fused material 136 of fused region 334 is disposed about a portion of core wire 56. In a presently preferred embodiment, fused material 136 of fused region 334 is adapted to retain core wire 56. Fused material 136 of fused region 334 also defines a plurality of transition region inflation lumens 138 and a guidewire lumen 104. In a presently preferred embodiment, transition region inflation lumens 138 are in fluid communication with first lumen 118 of first shaft portion 116 and second lumen 122 of second shaft portion 120.

Figure 8:
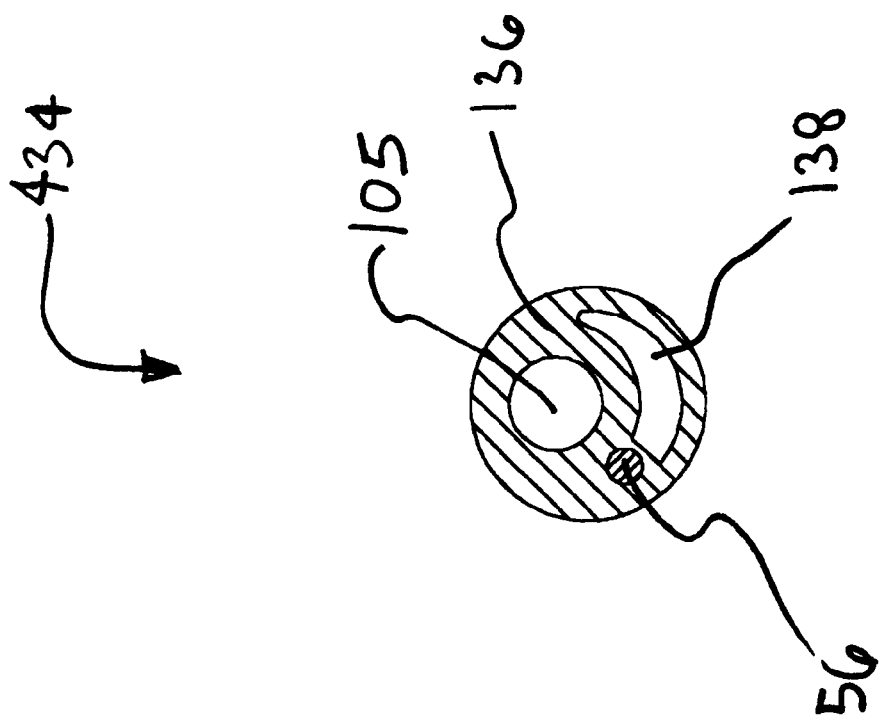
FIG. 8 is a cross sectional view of yet another embodiment of a fused region of a transition region of a catheter.

FIG. 8 is a cross sectional view of an additional embodiment of a fused region 434. In the embodiment of FIG. 8, core wire 56 is disposed in an offset position relative to transition region guidewire lumen 105. As in the previous embodiment, core wire 56 passes through fused region 434 and the material of fused region 434 is disposed about a portion of core wire 56. In the embodiment of FIG. 8, fused region 434 defines a transition region inflation lumen 138 which passes through fused region 434. In a presently preferred embodiment, transition region inflation lumen 138, first lumen 118, and second lumen 122 form a portion of inflation lumen 106 of catheter 100.

Figure 9:
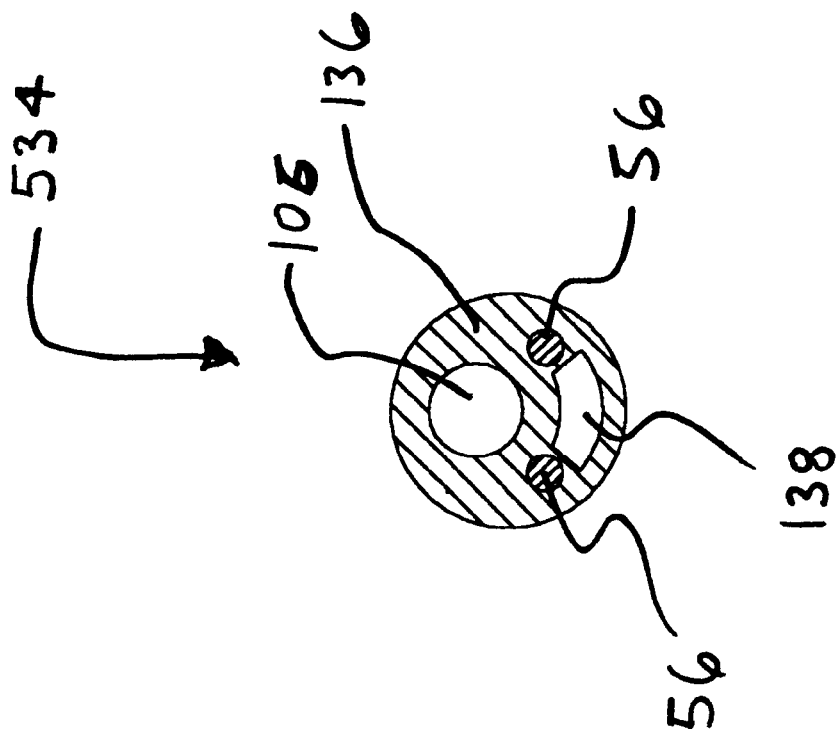
FIG. 9 is a cross sectional view of still another embodiment of a fused region of a transition region of a catheter.

FIG. 9 is a cross sectional view of an additional embodiment of a fused region 534. In the embodiment of FIG. 9, a plurality of core wires 56 pass through fused region 534. Fused material 136 defines a transition region inflation lumen 138 which passes through fused region 534 proximate core wires 56. Each core wire 56 is retained by fused material 136 of fused region 534. In a presently preferred embodiment, transition region inflation lumens 138 is in fluid communication with first lumen 118 of first shaft portion 116 and second lumen 122 of second shaft portion 120. Transition region inflation lumen 138, first lumen 118, and second lumen 122 may all form a portion of inflation lumen 106 of catheter 100.

Figure 10:
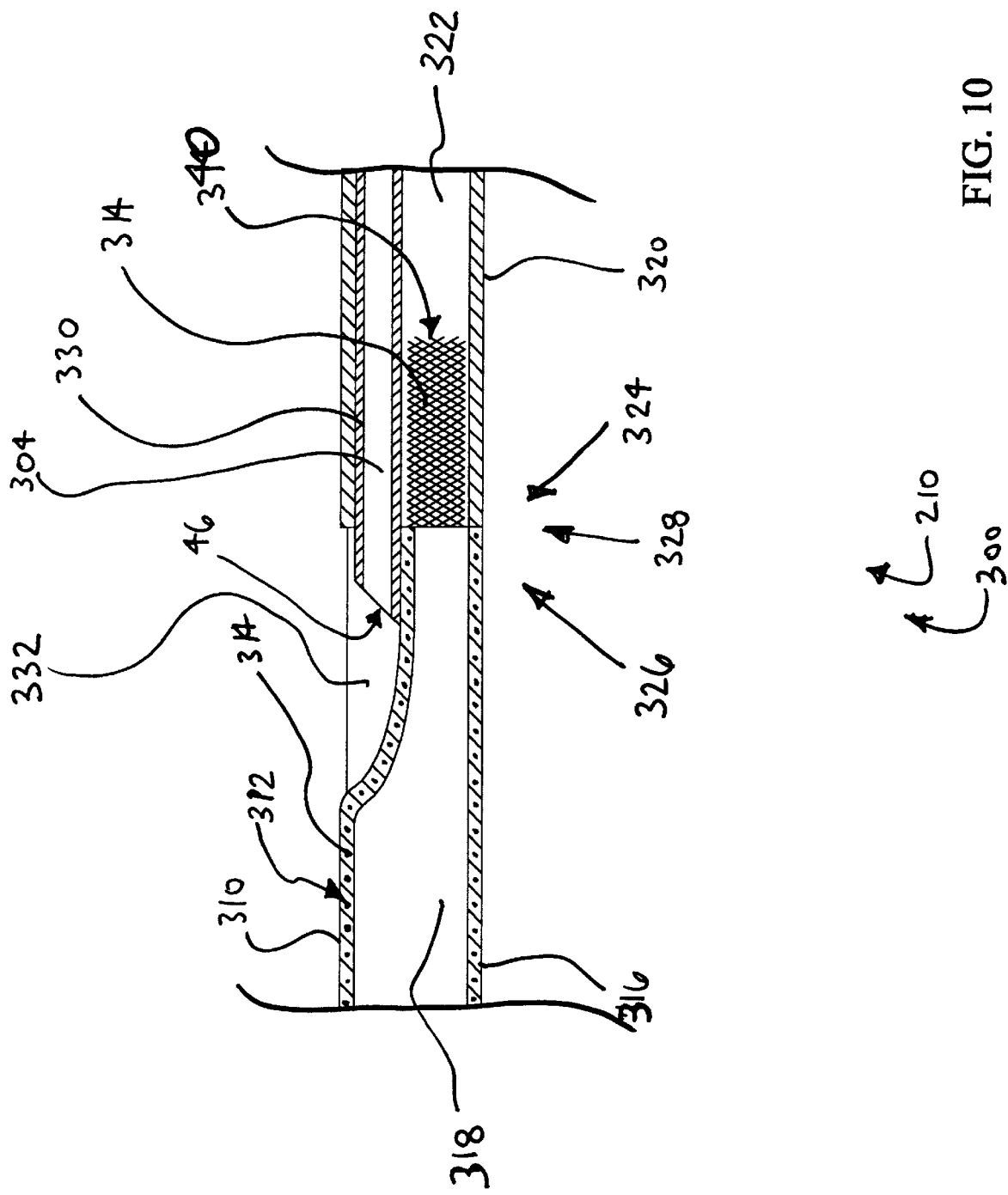
FIG. 10 is a cross-sectional view of an assembly in accordance with the present invention.

FIG. 10 is a cross-sectional view of an assembly 210 in accordance with the present invention. Assembly 210 includes a first shaft portion 316 having a first lumen 318 and a distal end 326. Assembly 210 also includes a second shaft portion 320 having a second lumen 322 and a proximal end 324. Distal end 326 of first shaft portion 316 is disposed proximate proximal end 324 of second shaft portion 320 forming a joint 328. In the embodiment of FIG. 10, joint 328 may be generally referred to as a butt joint.

In the embodiment of FIG. 10, first shaft portion 316 includes a jacket material 310 and a support member 312 comprising a plurality of filaments 314. A support matrix 340 comprising filaments 314 extending beyond jacket material 310 is disposed within second lumen 322 of second shaft portion 320. As shown in FIG. 10, filaments 314 extend across joint 328. In a presently preferred embodiment, filaments 314 are adapted to reinforce joint 328.

An inner tubular member or inner 330 is disposed proximate a crimp 332 formed in first shaft portion 316. As show in FIG. 10, a portion of inner 330 is disposed within second lumen 322 defined by second shaft portion 320. In a presently preferred embodiment, inner 330 defines a proximal guidewire port 46, a guidewire lumen 304, and a distal guidewire port 48 (not shown) of a catheter 300.

Figure 11:
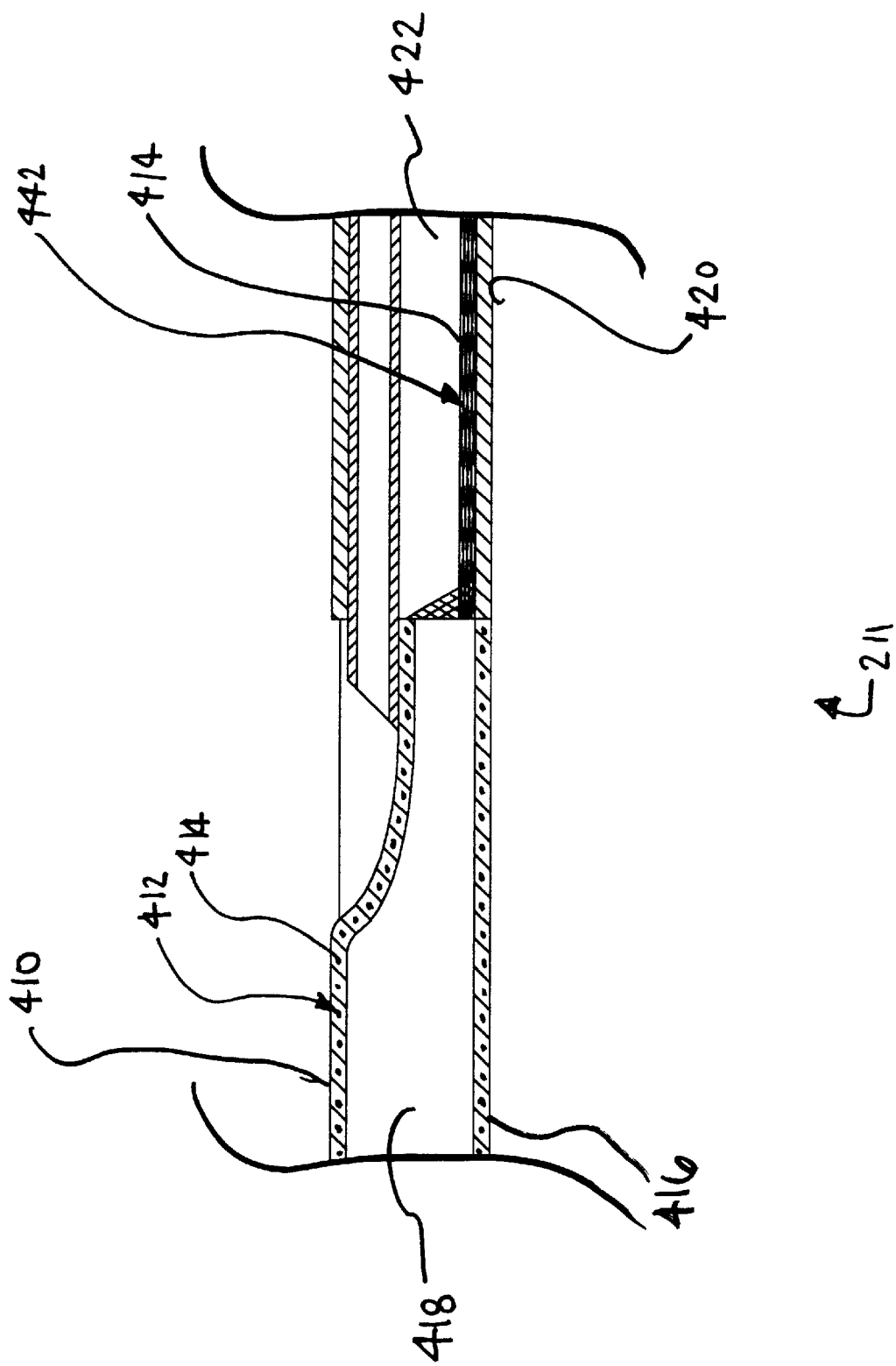
FIG. 11 is a cross-sectional view of an assembly in accordance with the present invention.

FIG. 11 is a cross-sectional view of an assembly 211 in accordance with the present invention. Assembly 211 includes a first shaft portion 416 having a first lumen 418 and a second shaft portion 420 having a second lumen 422. In the embodiment of FIG. 11, a support stem 442 is disposed within second lumen 422 of second shaft portion 420. Support stem 442 is comprised of filaments 414 of support member 412 extending beyond jacket material 410 of first shaft portion 416. In the embodiment of FIG. 11, filaments 414 of support stem 442 are arranged in a generally cylindrical shape to form support stem 442.

Figure 12:
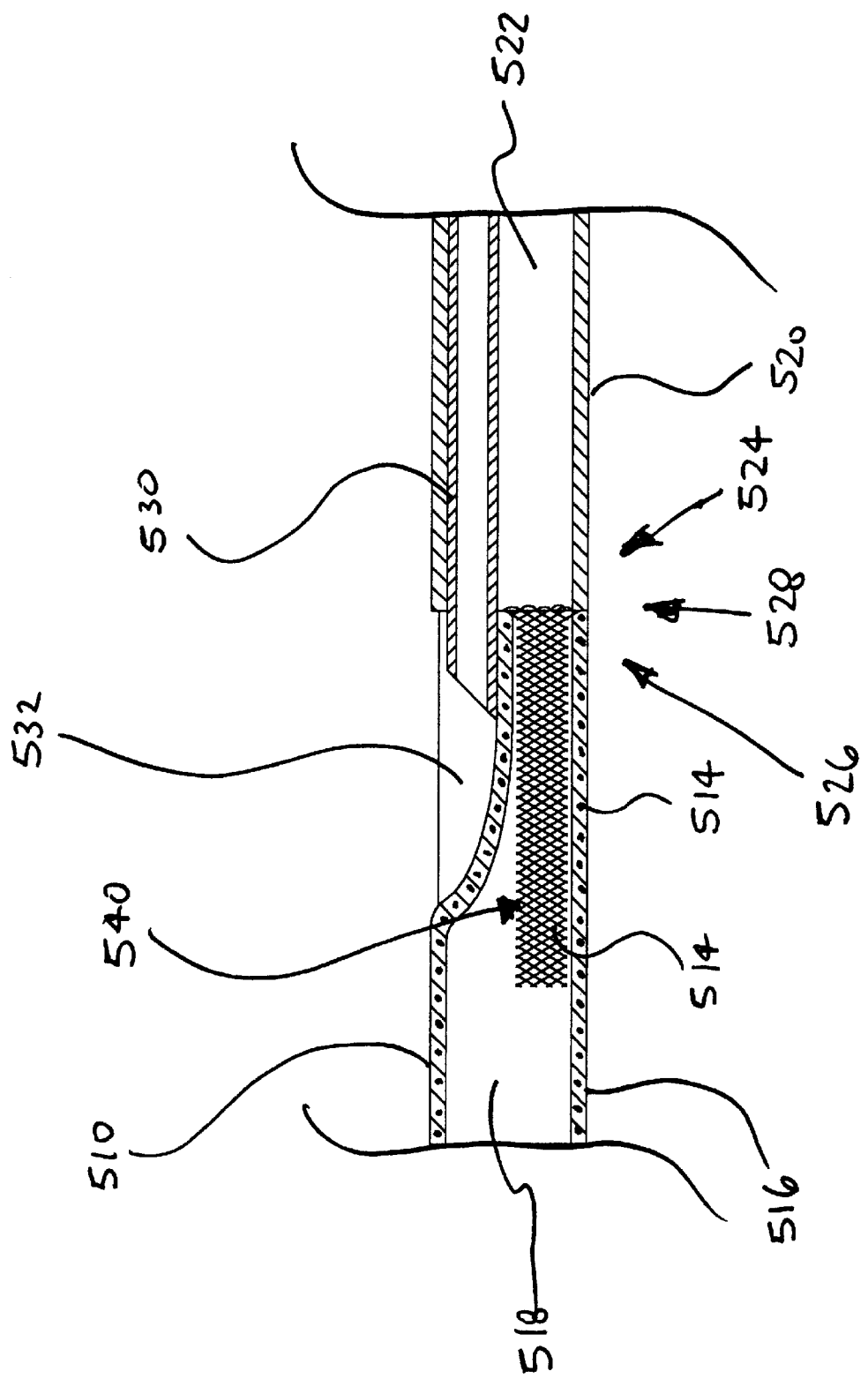
FIG. 12 is a cross-sectional view of an assembly in accordance with the present invention.

FIG. 12 is a cross-sectional view of an assembly 212 including a first shaft portion 516 defining a crimp 532 and having a first lumen 518. An inner 530 is disposed within crimp 532 of first shaft portion 516. A support matrix 540 is disposed within first lumen 518 proximate crimp 532. In a presently preferred embodiment, support matrix 540 is adapted to reinforce first shaft portion 516 proximate crimp 532. As shown in FIG. 12, support matrix 540 is comprised of filaments 514 extending beyond jacket material 510 of first shaft portion 516. Embodiments of assembly 212 have been envisioned in which support matrix 540 is comprised of filaments extending beyond a jacket material of second shaft portion 520. A distal end 526 of first shaft portion 516 is disposed proximate a proximal end 524 of second shaft portion 520 forming a joint 528. A portion of inner 530 is disposed within a second lumen 522 defined by second shaft portion 520.

Figure 13:
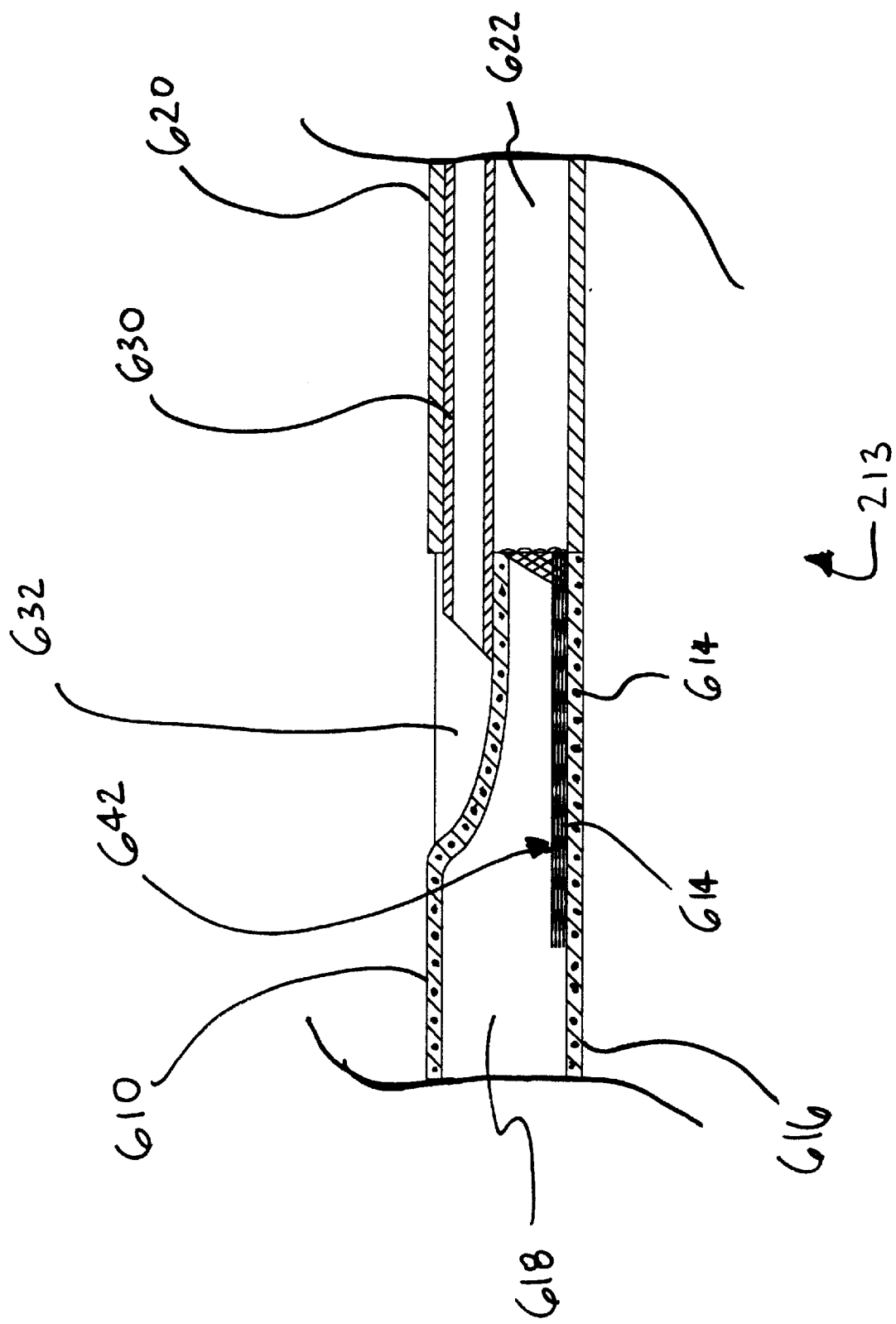
FIG. 13 is a cross-sectional view of an assembly in accordance with the present invention.

FIG. 13 is a cross-sectional view of an assembly 213 including a first shaft portion 616 having a first lumen 618 and a second shaft portion 620 having a second lumen 622. In the embodiment of FIG. 13, a support stem 642 is disposed within first lumen 618 of first shaft portion 616 proximate a crimp 632 formed in first shaft portion 616. Support stem 642 may stiffen a portion of first shaft portion 616 proximate crimp 632. Support stem 642 is comprised of a plurality filaments 614 extending beyond jacket material 610 of first shaft portion 616. In the embodiment of FIG. 13, filaments 614 of support stem 642 are arranged in a generally cylindrical shape to form support stem 642. Assembly 213 also includes an inner 630. A portion of inner 630 is disposed within second lumen 622 of second shaft portion 620. A portion of inner 630 extending beyond second shaft portion 620 is disposed proximate crimp 632 of first shaft portion 616.

Figure 14:
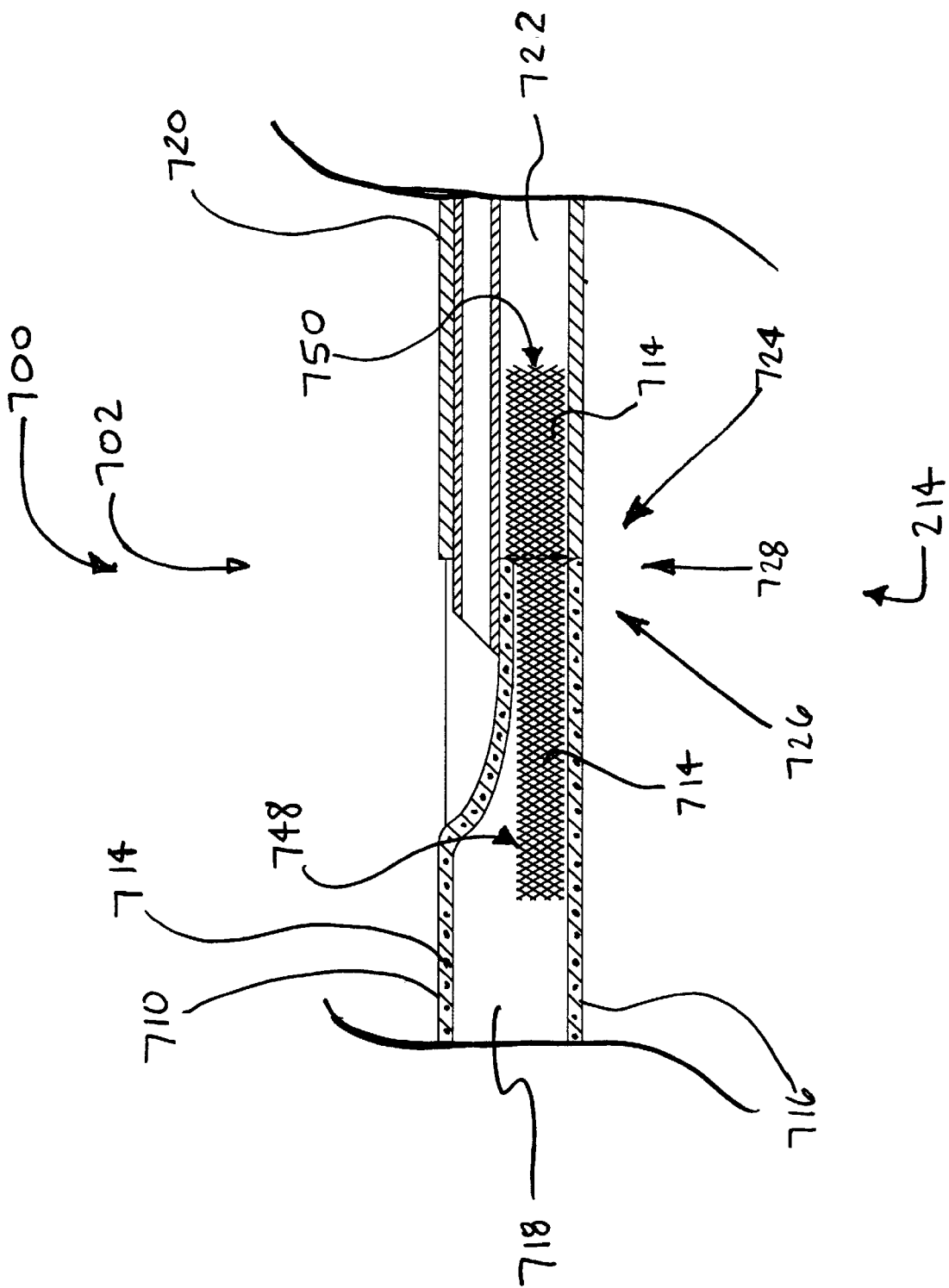
FIG. 14 is a cross-sectional view of an assembly in accordance with the present invention.

FIG. 14 is a cross-sectional view of an assembly 214 forming a transition region 702 of a catheter 700 in accordance with the present invention. Assembly 214 includes a first shaft portion 716 and a second shaft portion 720. A distal end 726 of first shaft portion 716 is disposed proximate a proximal end 724 of second shaft portion 720 forming a joint 728. A first support matrix 748 comprising a plurality of filaments 714 is disposed within a first lumen 718 of first shaft portion 716 proximate joint 728. A second support matrix 750 comprising a plurality of filaments 714 is disposed within a second lumen 722 of second shaft portion 720 proximate joint 728. In a presently preferred embodiment first support matrix 748 and second support matrix 750 provide support to transition region 702 and reinforce joint 728. In the embodiment of FIG. 14, filaments 714 comprising first support matrix 748 and second support matrix 750 extend beyond a jacket material 710 of first shaft portion 716. Embodiments of assembly 214 have been envisioned in which first support matrix 748 and/or second support matrix 750 are comprised of filaments extending beyond a jacket material of second shaft portion 720.

Figure 15:
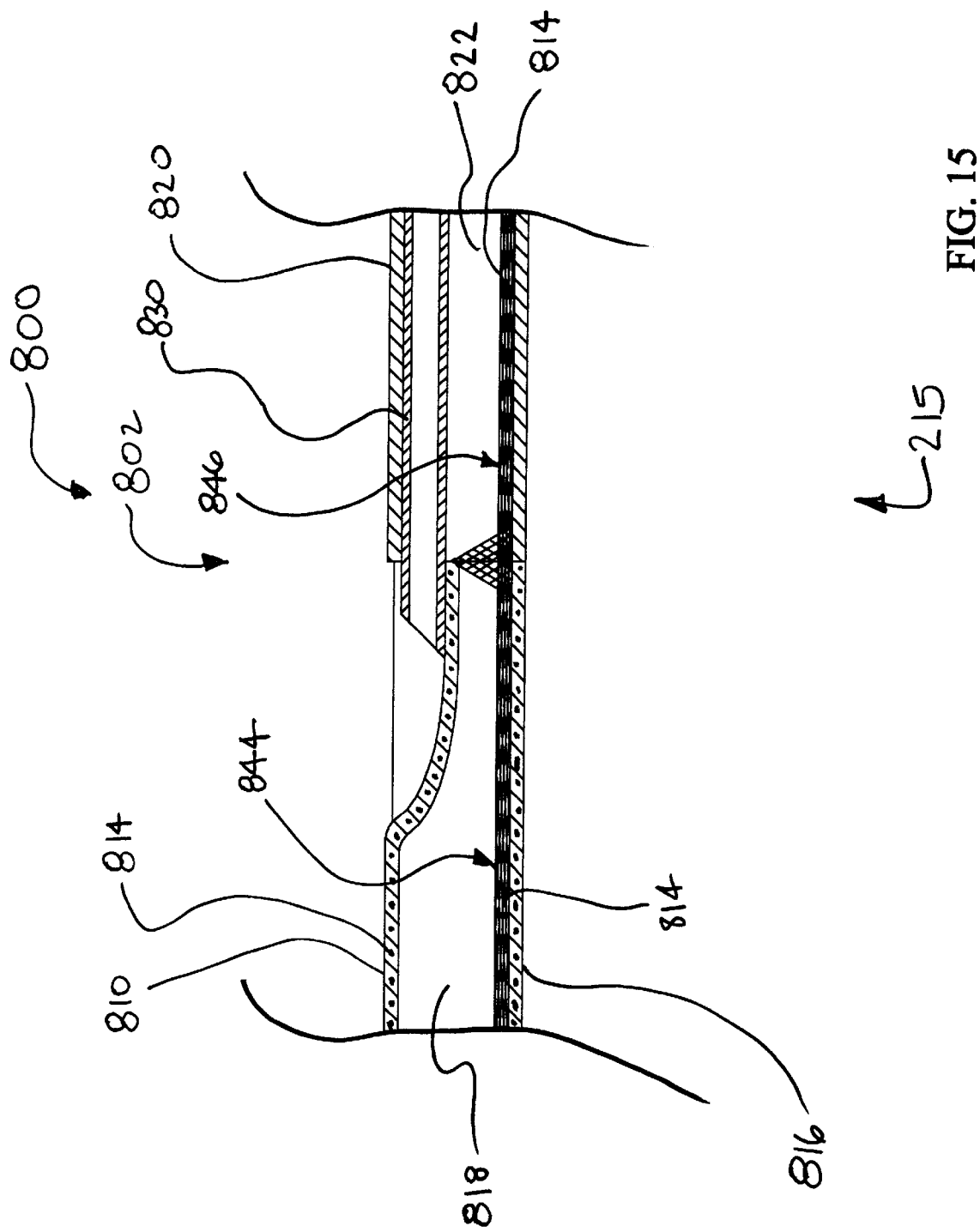
FIG. 15 is a cross-sectional view of an assembly in accordance with the present invention.

FIG. 15 is a cross-sectional view of an assembly 215 forming a transition region 802 of a catheter 800 in accordance with the present invention. Assembly 215 includes a first shaft portion 816 having a first lumen 818 and a second shaft portion 820 having a second lumen 822. A first support stem 844 is disposed within first lumen 818 of first shaft portion 816. A second support stem 846 and an inner 830 are both disposed within second lumen 822 of second shaft portion 820. Inner 830 extends beyond second shaft portion 820 and a portion of inner 830 is disposed proximate a crimp 832 formed by first shaft portion 816. First support stem 844 and second support stem 846 are comprised of a plurality filaments 814. In the embodiment of FIG. 14, filaments 814 beyond a jacket material 810 of first shaft portion 816. Embodiments of assembly 215 have been envisioned in which first support stem 844 and second support stem 846 are comprised of filaments extending beyond a jacket material of second shaft portion 820.

Figure 16:
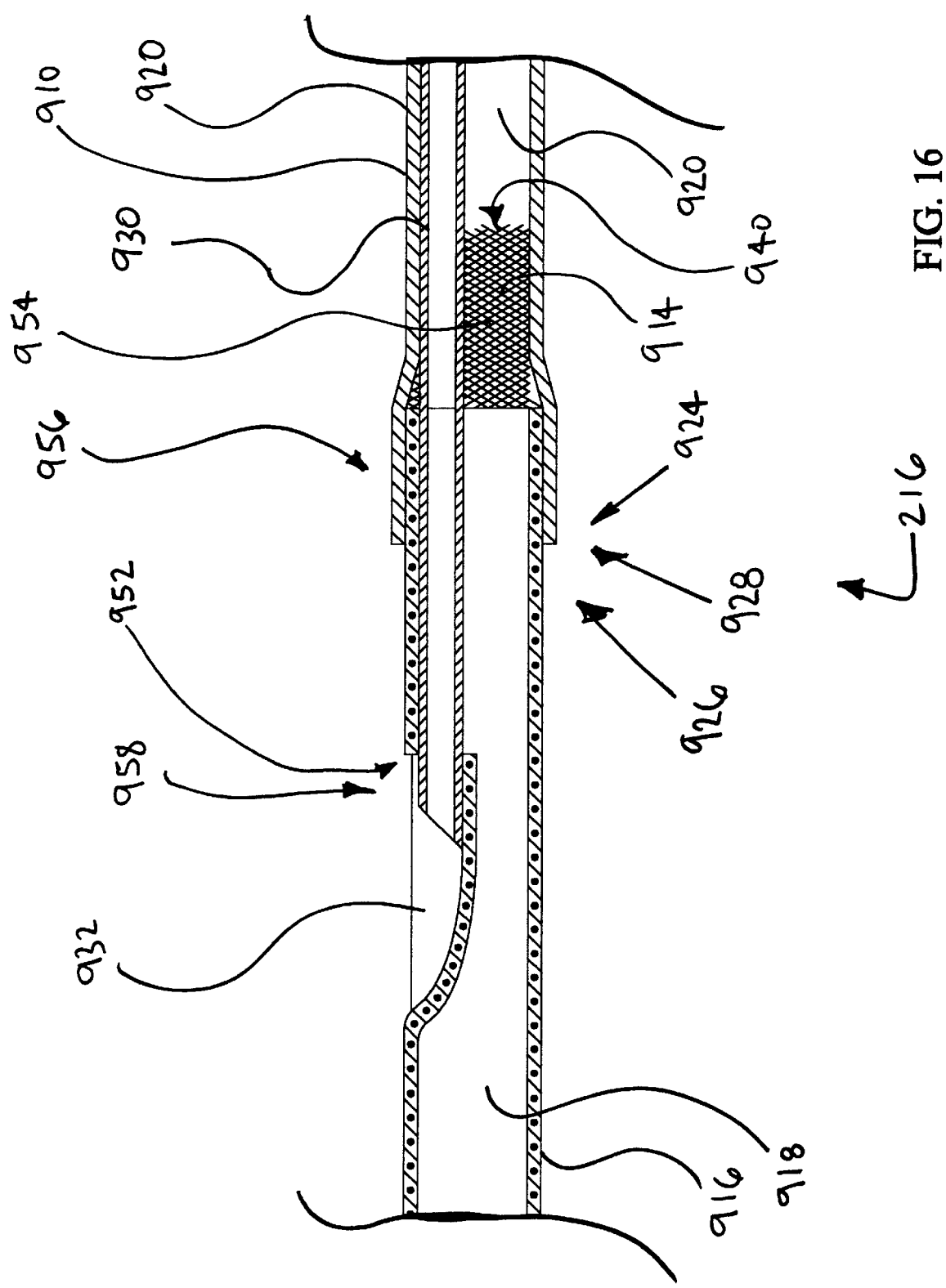
FIG. 16 is a cross-sectional view of an assembly including a crimped region and a joint region accordance with the present invention.

FIG. 16 is a cross-sectional view of an assembly 216 in accordance with the present invention. Assembly 216 includes a first shaft portion 916, a second shaft portion 920, and an inner 930. First shaft portion 916 includes a crimp 932 defining an opening 952. A proximal portion 958 of inner 930 passes through opening 952 and is disposed proximate crimp 932. Inner 930 is partially disposed within a first lumen 918 of first shaft portion 916 and a second lumen 922 of second shaft portion 920. Second shaft portion 920 includes an enlarged portion 956 proximate the proximal end 924 thereof. A distal end 926 of first shaft portion 916 has been inserted into enlarged portion 956 of second shaft portion 920 forming a joint 928. Joint 928 of FIG. 16 may be generally referred to as a lap joint. A method in accordance with the present invention may include the step of fusing material proximate joint 928 forming a bond between first shaft portion 916 and second shaft portion 920. A method in accordance with the present invention may also include the step of fusing material proximate crimp 932 forming a proximal guidewire port. As shown in FIG. 16, a support matrix 940 comprising a plurality of filaments 914 is disposed within second lumen 922 of second shaft portion 920. The presence of support matrix 940 disposed within second lumen 922 of second shaft portion 920 may increase the strength and stiffness joint 928. A method in accordance with the present invention may include the step of fusing material proximate joint 928. The step of fusing material, may result in a jacket material 910 of second shaft portion 920 being disposed within a plurality of interstitial openings 954 defined by support matrix 940. A method in accordance with the present invention may also include the step of fusing material proximate crimp 932.

Figure 17:
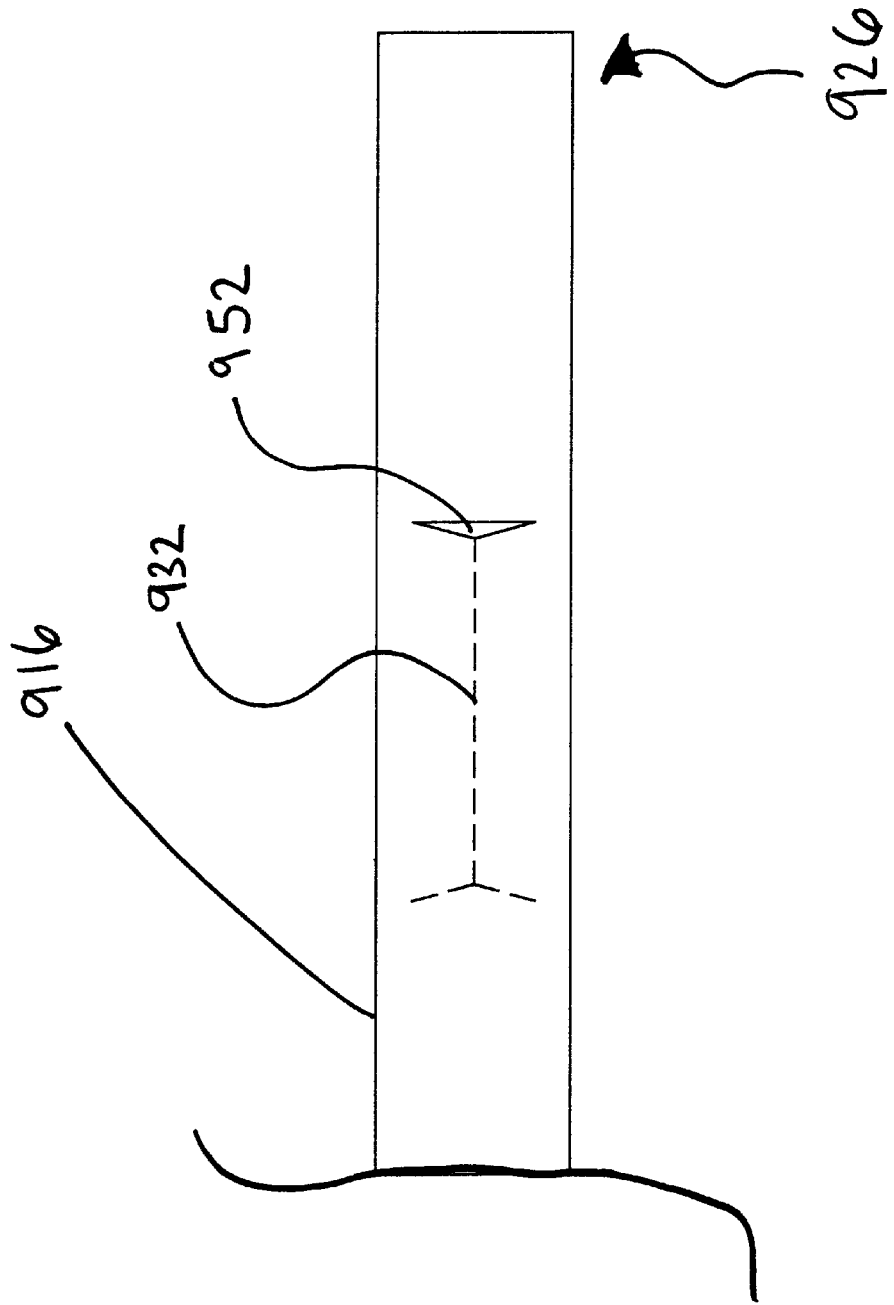
FIG. 17 is a plan view of first shaft portion including a crimp defining an opening.

FIG. 17 is a plan view of first shaft portion 916 of assembly 216 prior to its inclusion in assembly 216. FIG. 17 provides an additional view of crimp 932 of first shaft portion 916 and opening 952 defined by crimp 932.

Figure 18:
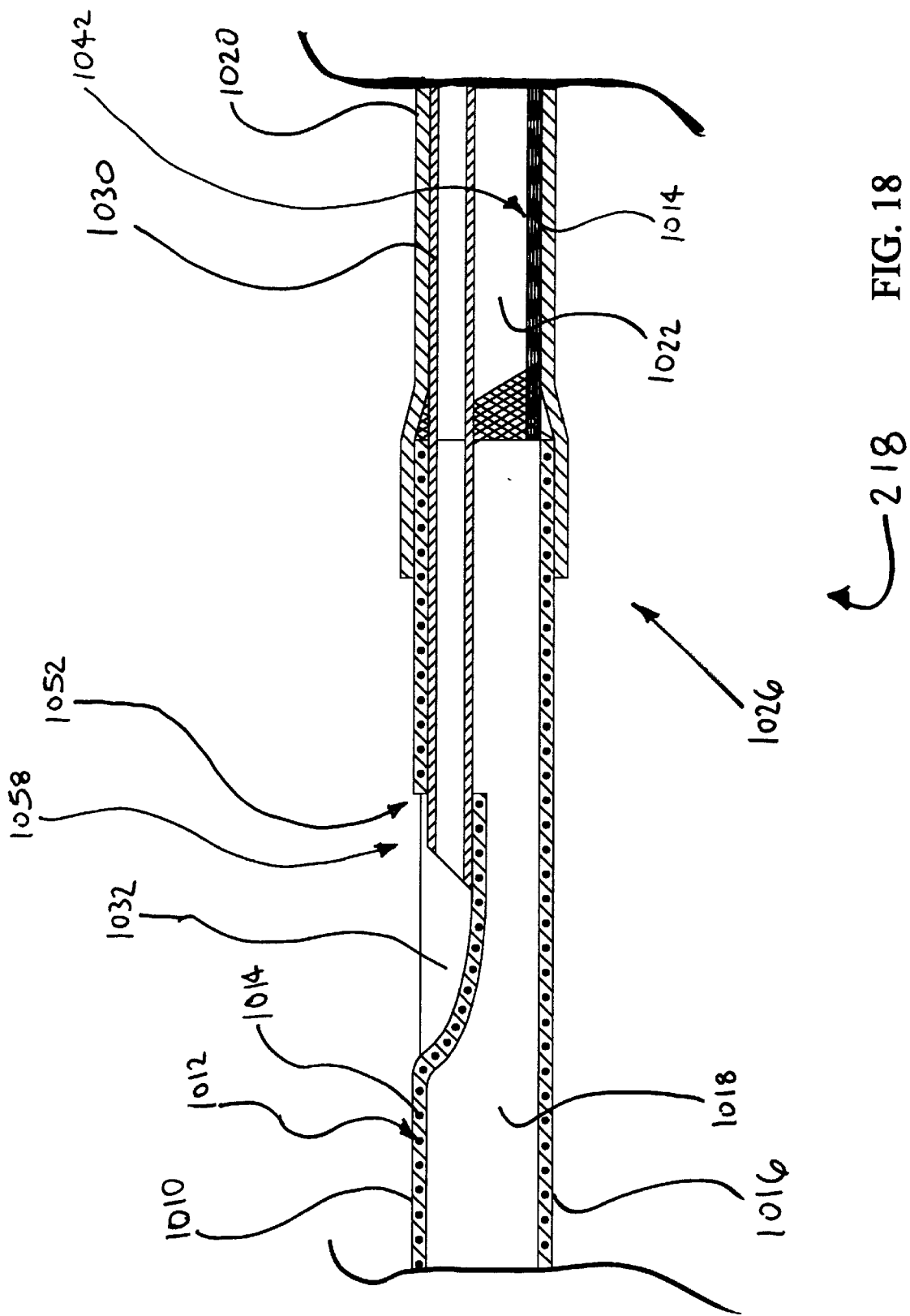
FIG. 18 is a cross-sectional view of an assembly including a crimped region and a joint region accordance with the present invention.

FIG. 18 is a cross-sectional view of an assembly 218 in accordance with the present invention. Assembly 218 includes a first shaft portion 1016, a second shaft portion 1020, and an inner 1030. First shaft portion 1016 includes a distal end 1026, first lumen 1018, a jacket material 1010, and a support member 1012 comprised of a plurality of filaments 1014. Filaments 1014 of support member 1012 extend beyond jacket material 1010 and form a support stem 1042. Support stem 1042 and distal end 1026 of first shaft portion 1016 have been inserted into a second lumen 1022 of second shaft portion 1020. First shaft portion 1016 also includes a crimp 1032 defining an opening 1052. A proximal portion 1058 of an inner 1030 passes through opening 1052 and is disposed proximate crimp 1032. The remainder of inner 1030 is disposed within a first lumen 1018 of first shaft portion 1016 and a second lumen 1022 of second shaft portion 1020. The presence of support stem within second lumen 1022 of second shaft portion 1020 may increase the stiffness of a portion of second shaft portion 1020.

Figure 19:
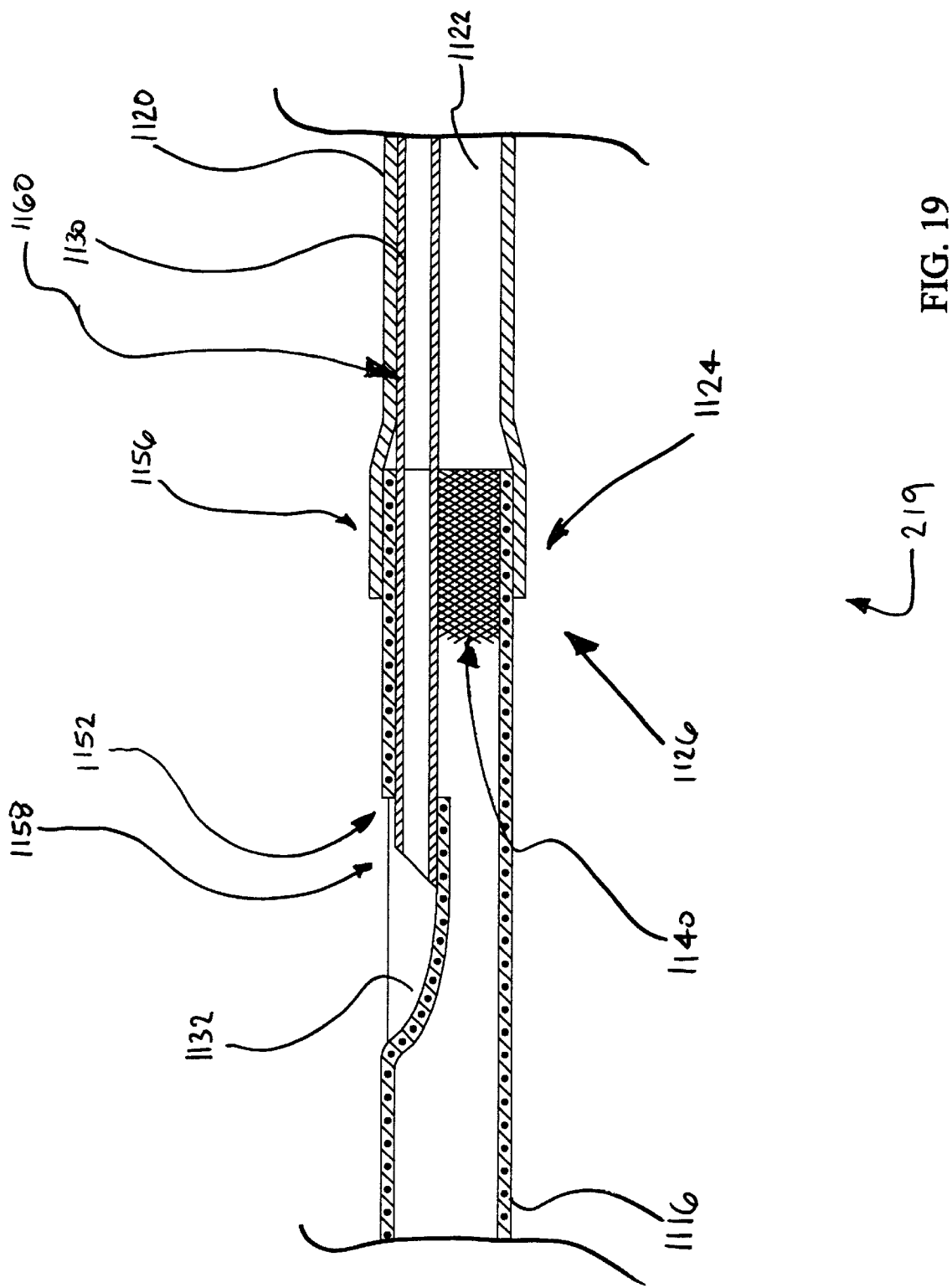
FIG. 19 is a cross-sectional view of an assembly including a crimped region and a joint region accordance with the present invention.

FIG. 19 is a cross-sectional view of an assembly 219 in accordance with the present invention. Assembly 219 includes a second shaft portion 1120 having a second lumen 1122 and an enlarged portion 1156 proximate a proximal end 1124 thereof. Assembly 219 also includes a first shaft portion 1116 having a distal end 1126 disposed within second lumen 1122 of second shaft portion 1120 proximate enlarged portion 1156. First shaft portion 1116 includes a crimp 1132 defining an opening 1152. A proximal portion 1158 of inner 1130 is disposed proximate crimp 1132. A remaining portion 1160 of inner 1130 passes through opening 1152 and is disposed within a first lumen 1118 of first shaft portion 1116 and second lumen 1122 of second shaft portion 1120. As shown in FIG. 19, a support matrix 1140 comprising a plurality of filaments is disposed within first lumen 1118 of first shaft portion 1116.

Figure 20:
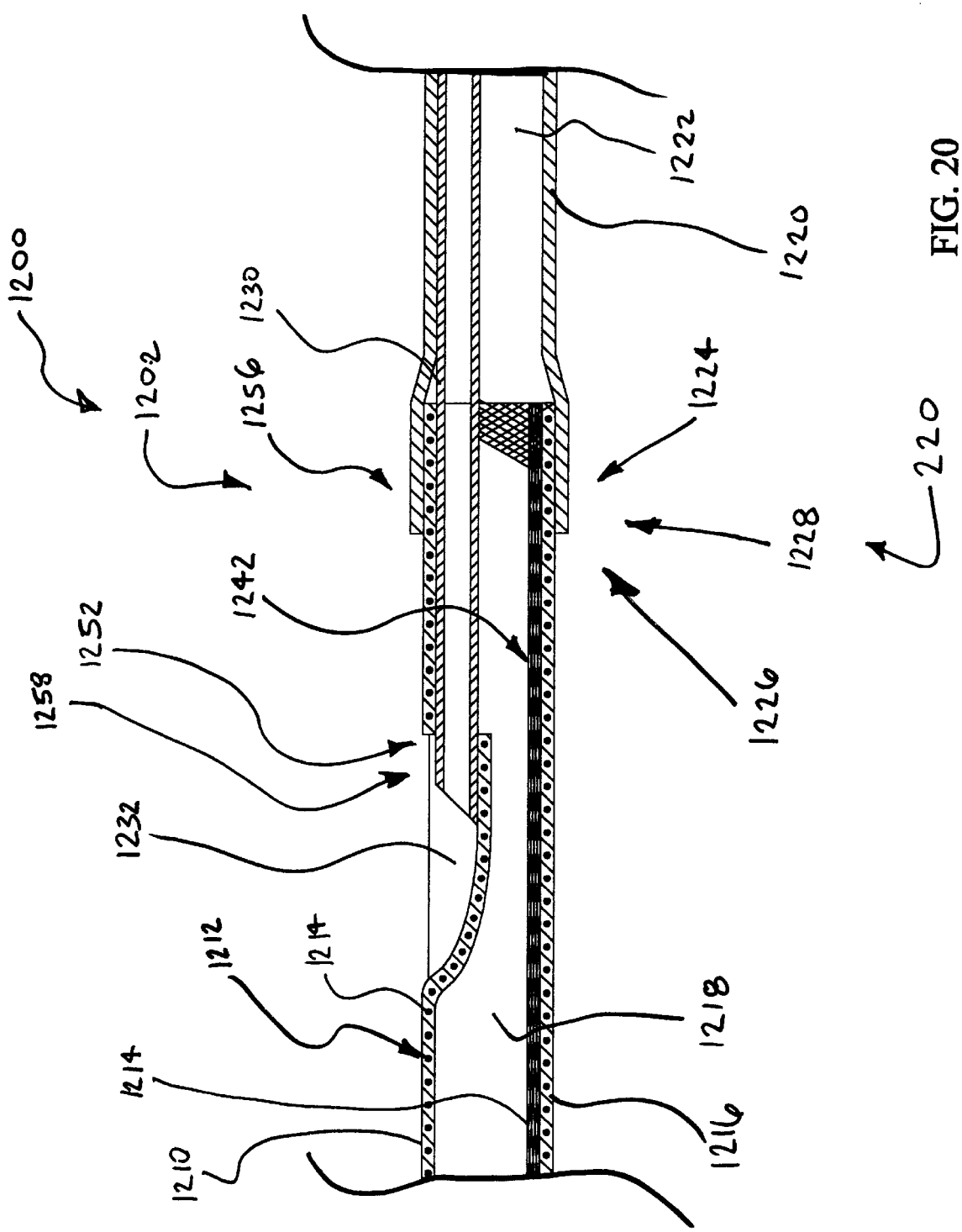
FIG. 20 is a cross-sectional view of an assembly including a crimped region and a joint region accordance with the present invention.

FIG. 20 is a cross-sectional view of an assembly 220 forming a transition region 1202 of a catheter 1200. Assembly 220 includes a first shaft portion 1216 having a support member 1212, a first lumen 1218 and a crimp 1232 defining an opening 1252 in fluid communication with first lumen 1218. An inner 1230 is partially disposed within first lumen 1218 of first shaft portion 1216. A proximal portion 1258 of inner 1230 passes through opening 1252 and is disposed proximate crimp 1232. A portion of inner 1230 is also disposed within a second lumen 1222 defined by a second shaft portion 1220. Second shaft portion 1220 includes an enlarged portion 1256 disposed proximate a proximal end 1224 thereof. A distal end 1226 of first shaft portion 1216 has been inserted into enlarged portion 1256 of second shaft portion 1220 forming a joint 1228. As shown in FIG. 20, a support stem 1242 is disposed within first lumen 1218 of first shaft portion 1216 proximate crimp 1232. Support stem 1242 is comprised of filaments 1214 of support member 1212 extending beyond a jacket material 1210 of first shaft portion 1216. In the embodiment of FIG. 20, filaments 1214 of support stem 1242 are arranged in a generally cylindrical shape to form support stem 1242. The presence of support stem within first lumen 1218 of first shaft portion 1216 may reduce the likelihood that catheter 1200 will kink proximate crimp 1232 of first shaft portion 1216.

Figure 21:
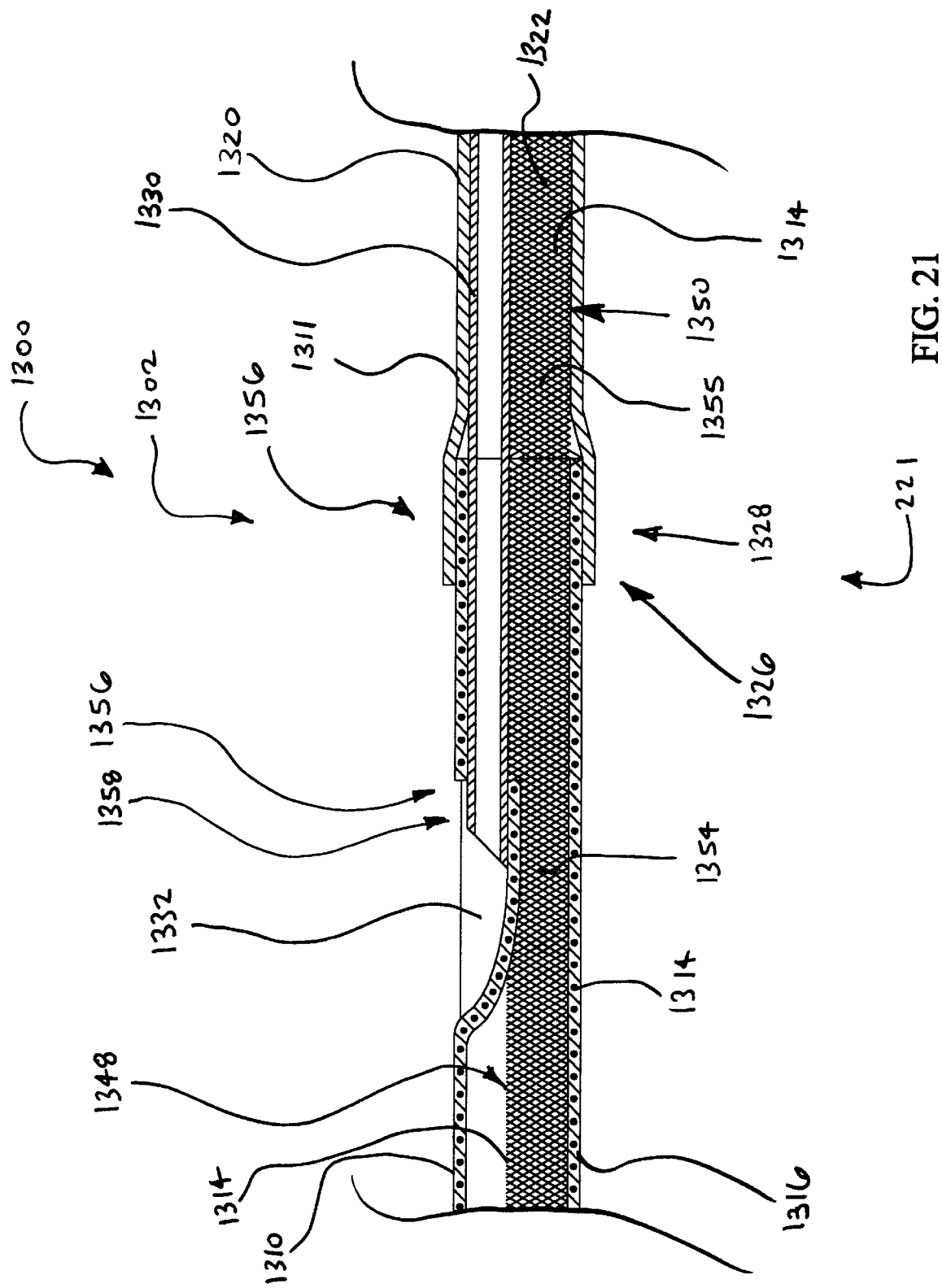
FIG. 21 is a cross-sectional view of an assembly including a crimped region and a joint region accordance with the present invention.

FIG. 21 is a cross-sectional view of an assembly 221 forming a transition region 1302 of a catheter 1300 in accordance with the present invention. Assembly 221 includes a second shaft portion 1320 having a second lumen 1322 and an enlarged portion 1356. A distal end 1326 of a first shaft portion 1316 is disposed within second lumen 1322 of second shaft portion 1320 proximate enlarged portion 1356 forming a joint 1328. First shaft portion 1316 includes a crimp 1332 defining an opening 1352. A proximal portion 1358 of an inner 1330 is disposed proximate crimp 1332. Inner 1330 passes through opening 1352 into first lumen 1318 of first shaft portion 1316. Inner 1330 extends beyond first shaft portion 1316 so that a portion of inner 1330 is disposed within second lumen 1322 of second shaft portion 1320. As shown in FIG. 21, a first support matrix 1348 comprising a plurality of filaments 1314 is disposed within first lumen 1318 of first shaft portion 1316. A second support matrix 1350 comprising a plurality of filaments 1314 is disposed within second lumen 1322 of second shaft portion 1320. In the embodiment of FIG. 21, filaments 1314 comprising first support matrix 1348 and second support matrix 1350 extend beyond a jacket material 1310 of first shaft portion 1316. Embodiments of assembly 221 are possible in which first support matrix 1348 and/or second support matrix 1350 are comprised of filaments extending beyond a jacket material of second shaft portion 1320. The presence of first support matrix 1348 disposed within first lumen 1318 of first shaft portion 1316 and second support matrix 1350 disposed within second lumen 1322 of second shaft portion 1320 may increase the strength of joint 1328. A method in accordance with the present invention may include the step of fusing material proximate joint 1328. The step of fusing material, may result in a jacket material 1310 of first shaft portion 1316 being disposed within interstitial openings 1354 defined by first support matrix 1348. A jacket material 1311 of second shaft portion may be disposed within interstitial openings 1353 defined by second support matrix 1350. A method in accordance with the present invention may also include the step of fusing material proximate crimp 1332.

Figure 22:
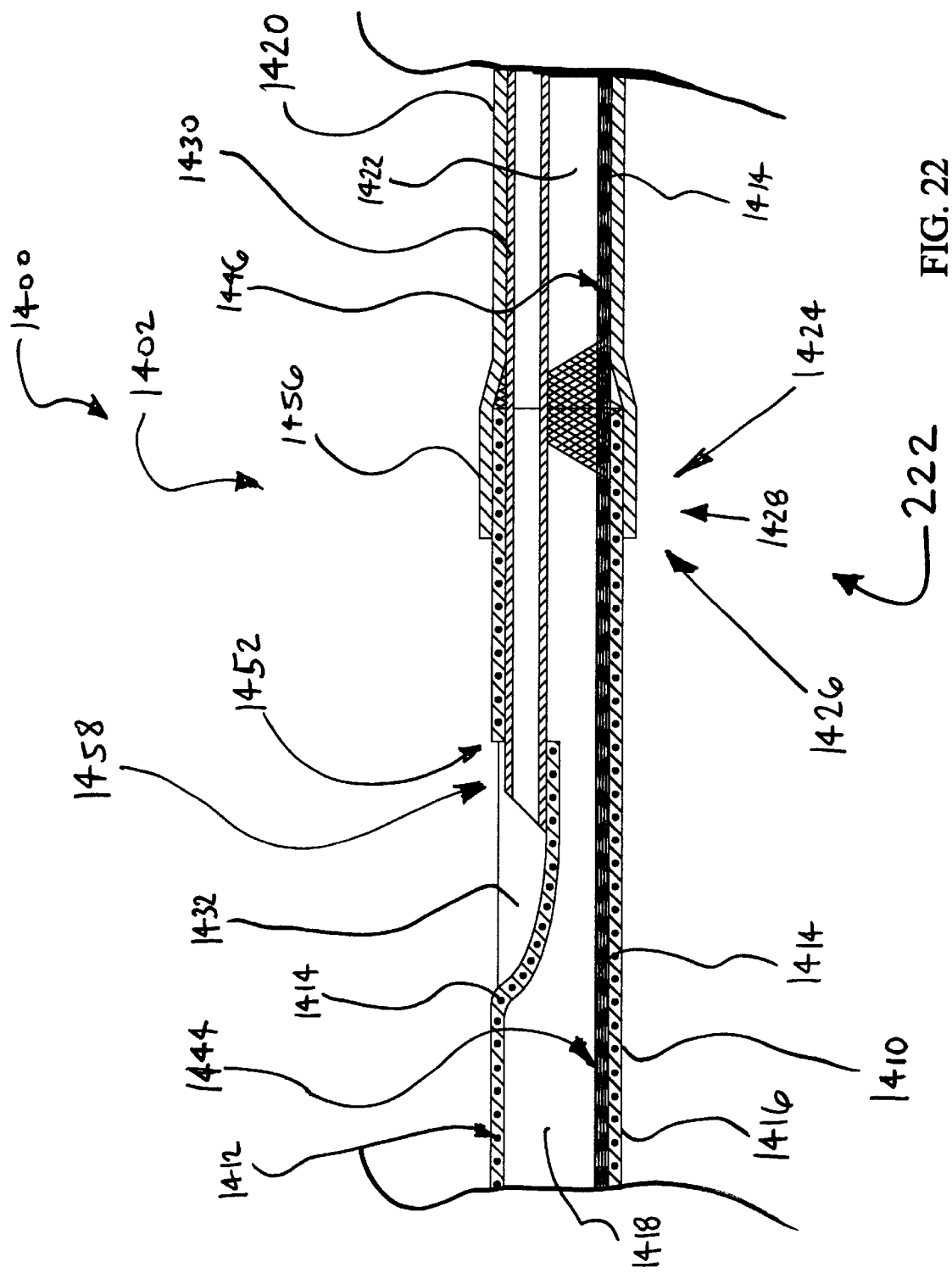
FIG. 22 is a cross-sectional view of an assembly including a crimped region and a joint region in accordance with the present invention.

FIG. 22 is a cross-sectional view of an assembly 222 forming a transition region 1402 of a catheter 1400 in accordance with the present invention. Assembly 222 includes a first shaft portion 1416, a second shaft portion 1420, and an inner 1430. First shaft portion 1416 includes a crimp 1432 defining an opening 1452. A proximal portion 1458 of inner 1430 passes through opening 1452 and is disposed proximate crimp 1432. Inner 1430 is partially disposed within a first lumen 1418 of first shaft portion 1416 and a second lumen 1422 of second shaft portion 1420. A proximal end 1424 of second shaft portion 1420 includes an enlarged portion 1456. A distal end 1426 of first shaft portion 1416 has been inserted into enlarged portion 1456 of second shaft portion 1420 forming a joint 1428. As shown in FIG. 22, a first support stem 1444 is disposed within first lumen 1418 of first shaft portion 1416 and a second support stem 1446 is disposed within second lumen 1422 of second shaft portion 1420. First support stem 1444 and second support stem 1446 are each comprised of filaments 1414 of support member 1412 extending beyond jacket material 1410 of first shaft portion 1416. The presence of first support stem within first lumen 1418 of first shaft portion 1416 may enhance the stiffness of catheter 1400 proximate transition region 1402.

Having thus described the figures, a method in accordance with the present invention may know be described with reference thereto. It should be understood that steps may be omitted from this process and/or the order of the steps may be changed without deviating from the spirit or scope of the invention. It is anticipated that in some applications, two or more steps may be performed essentially simultaneously to promote efficiency.

A method in accordance with the present invention may begin with the step of providing a first shaft portion, and a second shaft portion. The step of providing these shaft portions may include the step of forming a shaft portion having a lumen, a supporting member, and a layer of jacket material. The process of forming a shaft portion may include the steps of winding braiding, or knitting a plurality of filaments around an inner tube to form a support member. A layer of jacket material may then be formed over both the inner tube and the support member. In one method in accordance with the present invention, the step of forming the layer of jacket material includes the step of extruding a molten thermoplastic material onto the combined layers of the inner tube and the support member. When this process is used, the jacket material may fill any interstitial spaces in the support member.

A process in accordance with the present invention may include the step of stripping away a portion of the jacket material covering the filaments of the support member. The filaments may then be arranged to form one or more support elements. Many embodiments of a support element are possible without deviating from the spirit and scope of the present invention. Examples of support elements include a support matrix, and a support stem. One or more support elements may be inserted into a first lumen defined by the first shaft portion.

A crimp may be formed in the first shaft portion and a proximal portion of an inner may be laid in a position proximate the crimp. A distal portion of the inner may be inserted into a second lumen defined by the second shaft portion. One or more support elements may also be inserted into the second lumen defined by the second shaft portion. A distal portion of the first shaft portion may then be placed proximate a proximal portion of the second shaft portion forming an assembly having a joint. Many embodiments of a joint are possible without deviating from the spirit and scope of the present invention. Examples of joints which may be suitable in some applications include lap joints and butt joints.

A method in accordance with the present invention may also include the step of selectively heating one or more portions of the assembly to create one or more fused regions. In a presently preferred method, the selective heating of portions of the assembly is accomplished by illuminating selected portions of the assembly with a LASER. In one method in accordance with the present invention, the assembly is rotated while a portion thereof is illuminated with a LASER. In one method in accordance with the present invention, a portion of the material heated during the selective heating step flows into a plurality of interstitial spaces defined by the filaments of the support element.

Those of skill in the art will appreciate that other methods of selectively heating a portion of the assembly are possible without deviating from the spirit and scope of the present invention. Heating methods which may be suitable in some applications include convection heating, conduction heating, and radiation. An example of heating with radiant energy is directing infrared energy from an infrared heat source at the material. Infrared energy sources suitable for this process are commercially available from Research Incorporated of Minnetonka, Minn. An example of heating with conduction is touching the desired area with a heated tool. Electric heaters suitable for heating a heated tool are commercially available from Watlow Incorporated of St. Louis, Mo. An example of heating with convection is placing the assembly in a temperature chamber. Temperature chambers suitable for this process are commercially available from Thermotron Corporation of New Holland, Mich.

A mandrel may be inserted in the lumen of the inner to reduce the likelihood that this lumen will be closed during the selective heating step. One or more mandrels may also be inserted into the first lumen defined by the first tubular member and the second lumen defined by the second tubular member. In one method in accordance with the present invention a plurality of mandrels are utilized to define a plurality of transition region inflation lumens within the material fused during the selective heating process. In another method in accordance with the present invention, a plurality of mandrels are utilized to position a core wire within the transition region of the catheter.

It should be understood that steps may be omitted from this process and the order of the steps may be changed without deviating from the spirit or scope of the invention. Additional steps have also have been envisioned. For example, one envisioned method includes the step of overlaying the assembly with a sleeve. The sleeve may be PTFE shrink tubing. Suitable PTFE shrink tubing is commercially available Zeus Industries of Orangeburg, S.C. and Raychem Corporation of Menlo Park, Calif.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method of bonding tubular members, the method comprising the steps of;
   providing a first generally tubular member having a bonding portion disposed proximate a bonding end thereof, an ancillary end, and a lumen extending therethrough;
   the first tubular member including a support member encased in a substrate material;
   the support member having a plurality of filaments;
   providing a second generally tubular member having a bonding portion disposed proximate a bonding end thereof, an ancillary end, and a lumen extending therethrough;
   stripping a portion of the substrate material of the first tubular member from the filaments of the support member of the first tubular member proximate the bonding portion thereof to create a plurality of exposed filaments;
   dividing the exposed filaments into a first group and a second group;
   forming a first array comprising the exposed filaments of the first group;
   forming a second array comprising the exposed filaments of the second group;
   inserting the first array into the lumen of the first tubular member;
   inserting the second array into the lumen of the second tubular member;
   positioning the bonding portion of the first tubular member proximate the bonding portion of the second tubular member; and
   heating the bonding portion of the first tubular member and the bonding portion of the second tubular member to form a bond therebetween.

2. The method of claim 1, further including the step of filling a plurality of interstitial spaces defined by the second array with the substrate material of the second tubular member.

3. The method of claim 1, further including the step of filling a plurality of interstitial spaces defined by the first array with the substrate material of the first tubular member.

4. The method of claim 1, wherein the step of heating the bonding portion of the first tubular member and the bonding portion of the second tubular member includes the step of exposing the bonding portion of the first tubular member and the bonding portion of the second tubular member to electromagnetic waves.

5. The method of claim 1, wherein the step of heating the bonding portion of the first tubular member and the bonding portion of the second tubular member includes the step of exposing the bonding portion of the first tubular member and the bonding portion of the second tubular member to a hot fluid.

6. The method of claim 1, wherein the step of heating the bonding portion of the first tubular member and the bonding portion of the second tubular member includes the step of illuminating the bonding portion of the first tubular member and the bonding portion of the second tubular member with a laser beam.

7. The method of claim 1, wherein the step of heating the bonding portion of the first tubular member and the bonding portion of the second tubular member includes the steps of rotating the first tubular member and the second tubular member and illuminating the bonding portion of the first tubular member and the bonding portion of the second tubular member with a laser beam.

8. The method of claim 1, further including the step of arranging the exposed filaments of the first array to form a first stem.

9. The method of claim 1, further including the step of step of twisting together the exposed filaments of the first stem to form a first stem.

10. The method of claim 1, further including the step of arranging the exposed filaments of the second array to form a second stem.

11. A method of bonding tubular members to form a catheter shaft segment having a guidewire port, the method comprising the steps of:
    providing a first generally tubular member having a bonding portion disposed proximate a bonding end thereof, an ancillary end, and a lumen extending therethrough;
    the first tubular member including a support member encased in a substrate material;
    the support member having a plurality of filaments;
    providing a second generally tubular member having a bonding portion disposed proximate a bonding end thereof, an ancillary end, and a lumen extending therethrough;
    providing an inner member having a proximal end, a distal end, and a lumen extending therebetween;
    stripping a portion of the substrate material of the first tubular member from the filaments of the support member of the first tubular member proximate the bonding portion thereof to create a plurality of exposed filaments;
    crimping the first tubular member proximate its bonding portion to form a recess;
    positioning the proximal end of a lumen member adjacent to the recess of the first tubular member;
    inserting the distal end of the lumen member into the lumen of the second tubular member;
    inserting at least a portion of the exposed filaments into the lumen of the second tubular member;
    positioning the bonding portion of the first tubular member proximate the bonding portion of the second tubular member; and heating the bonding portion of the first tubular member and the bonding portion of the second tubular member to form a bond therebetween.

12. The method of claim 11, further including the step of filling a plurality of interstitial spaces defined by the exposed filaments with the substrate material of the second tubular member.

13. The method of claim 11, wherein the step of heating the bonding portion of the first tubular member and the bonding portion of the second tubular member includes the step of exposing the bonding portion of the first tubular member and the bonding portion of the second tubular member to electromagnetic waves.

14. The method of claim 11, wherein the step of heating the bonding portion of the first tubular member and the bonding portion of the second tubular member includes the step of exposing the bonding portion of the first tubular member and the bonding portion of the second tubular member to a hot fluid.

15. The method of claim 11, wherein the step of heating the bonding portion of the first tubular member and the bonding portion of the second tubular member includes the step of illuminating the bonding portion of the first tubular member and the bonding portion of the second tubular member with a laser beam.

16. The method of claim 11, further including the step of arranging the exposed filaments to form a stem.

* * * * *